(12) United States Patent
Rohloff

(10) Patent No.: US 10,634,679 B2
(45) Date of Patent: Apr. 28, 2020

(54) COMPOUNDS AND METHODS FOR THE SYNTHESIS OF 5-(N-PROTECTED-TRYPTAMINOCARBOXYAMIDE)-2'-DEOXYURIDINE PHOSPHORAMIDITE FOR INCORPORATION INTO A NUCLEIC ACID

(71) Applicant: SOMALOGIC, INC., Boulder, CO (US)

(72) Inventor: John Rohloff, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 10 days.

(21) Appl. No.: 16/078,859

(22) PCT Filed: Mar. 13, 2017

(86) PCT No.: PCT/US2017/022007
§ 371 (c)(1),
(2) Date: Aug. 22, 2018

(87) PCT Pub. No.: WO2017/160672
PCT Pub. Date: Sep. 21, 2017

(65) Prior Publication Data
US 2019/0031702 A1  Jan. 31, 2019

Related U.S. Application Data

(60) Provisional application No. 62/308,132, filed on Mar. 14, 2016.

(51) Int. Cl.
| | | |
|---|---|---|
| C07H 19/073 | (2006.01) | |
| C07H 19/10 | (2006.01) | |
| G01N 33/574 | (2006.01) | |
| C07H 21/04 | (2006.01) | |
| C07D 209/16 | (2006.01) | |
| C07D 209/24 | (2006.01) | |
| C07H 1/00 | (2006.01) | |
| G06T 7/00 | (2017.01) | |

(52) U.S. Cl.
CPC ..... *G01N 33/57484* (2013.01); *C07D 209/16* (2013.01); *C07D 209/24* (2013.01); *C07H 1/00* (2013.01); *C07H 19/073* (2013.01); *C07H 19/10* (2013.01); *C07H 21/04* (2013.01); *G01N 33/57407* (2013.01); *G06T 7/0012* (2013.01); *G01N 2333/4727* (2013.01); *G06T 2207/30024* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 5,945,527 A | * | 8/1999 | Tu .......................... C07H 19/06 536/27.6 |
| 8,759,502 B2 | | 6/2014 | Fujihara |
| 9,353,142 B2 | | 5/2016 | Fujihara |
| 2015/0141637 A1 | | 5/2015 | Leumann et al. |
| 2015/0275283 A1 | | 10/2015 | Gall et al. |
| 2015/0353594 A1 | | 12/2015 | Lunstad et al. |

FOREIGN PATENT DOCUMENTS

| | | |
|---|---|---|
| AU | 2013202528 B2 | 5/2013 |
| WO | 2015048084 A1 | 4/2015 |

OTHER PUBLICATIONS

Vaught et al., "Expanding the Chemistry of DNA for in Vitro Selection," J. Am. Chem. Soc. 132(12):4141-4151, 2010.
International Search Report and Written Opinion issued in PCT/US2017/022007, dated May 10, 2017, 16 pages.
Liang, Yong, "Novel Approaches for the Synthesis of C-5 Modified Pyrimidine Nucleosides," FIU Electronic Theses and Dissertations, Paper 1591, 2014.

* cited by examiner

*Primary Examiner* — Traviss C McIntosh, III
(74) *Attorney, Agent, or Firm* — McNeill Baur PLLC

(57) ABSTRACT

Modified Tryptamine, Tryptamine-2'-deoxy-uridine (TrpdU) and TrpdU-phosphoramidites for oligonucleotide synthesis are provided, as well as improved methods of their synthesis and oligonucleotides comprising at least one modified TrpdU nucleotide.

26 Claims, 5 Drawing Sheets

(1)
N-α-BOC-tryptamine

Alkaline Oligo
Deprotection Conditions

N-1-Protected

COMPOUNDS AND METHODS FOR THE SYNTHESIS OF 5-(N-PROTECTED-TRYPTAMINOCARBOXYAMIDE)-2'-DEOXYURIDINE PHOSPHORAMIDITE FOR INCORPORATION INTO A NUCLEIC ACID

CROSS-REFERENCE TO RELATED APPLICATIONS

This application is a national phase entry pursuant to 35 U.S.C. § 371 of International Application No. PCT/US2017/022007, filed Mar. 13, 2017, which claims the benefit of priority of U.S. Provisional Application No. 62/308,132, filed Mar. 14, 2016, each of which is incorporated by reference herein in its entirety for any purpose.

FIELD

This disclosure relates to the field of modified bases, nucleotides, and phosphoramidites, including improved methods of synthesis and oligonucleotides comprising the modified nucleotides.

BACKGROUND

The chemically modified nucleotide, TrpdU (and its 2'-modified analogs), which bears a 3-(2-aminoethyl)-indole side chain, is useful, for example, in developing high-affinity aptamers to target analytes, such as proteins. The indole ring of TrpdU is electron-rich and polarizable, which may facilitate formation of secondary structure and complementary hydrophobic interfaces with target analytes. To date, TrpdU has not performed as well as other modified nucleotides as a phosphoramidite reagent in solid-phase oligonucleotide synthesis, and its use has therefore been limited.

There remains a need in the art for an improved TrpU phosphoramidite, and improved methods of making a TrpU phosphoramidite.

SUMMARY

In some embodiments, a compound having the structure

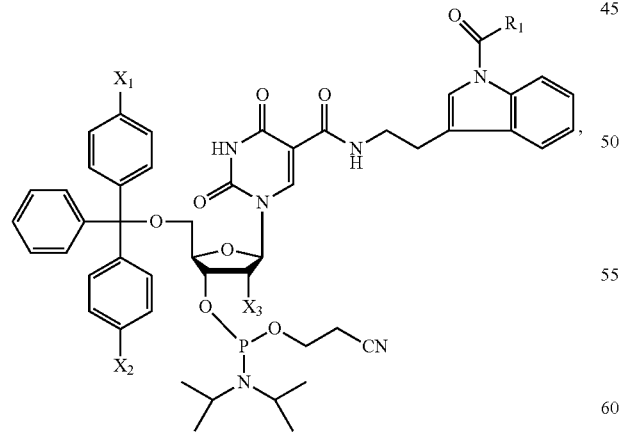

or a salt thereof, is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $X_1$ and $X_2$ are each independently selected from methoxy and hydrogen. In some embodiments, $X_3$ is selected from a methoxy, fluoro, hydrogen, and tert-butyldimethylsilyloxy.

In some embodiments, $R_1$ is tert-butyl. In some embodiments, $R_1$ is 1,1-dimethyl-propyl. In some embodiments, $R_1$ is 1,1-dimethyl-butyl; 2-chlorophenyl. In some embodiments, $R_1$ is 2-cyanophenyl. In some embodiments, $R_1$ is 1-methyl-cyclopentyl. In some embodiments, $R_1$ is 1-methyl-cyclohexyl. In some embodiments, $X_1$ and $X_2$ are methoxy. In some embodiments, $X_3$ is hydrogen. In some embodiments, $X_3$ is methoxy. In some embodiments, $X_3$ is fluoro. In some embodiments, $X_3$ is tert-butyldimethylsilyloxy.

In some embodiments, a compound provided herein is selected from:

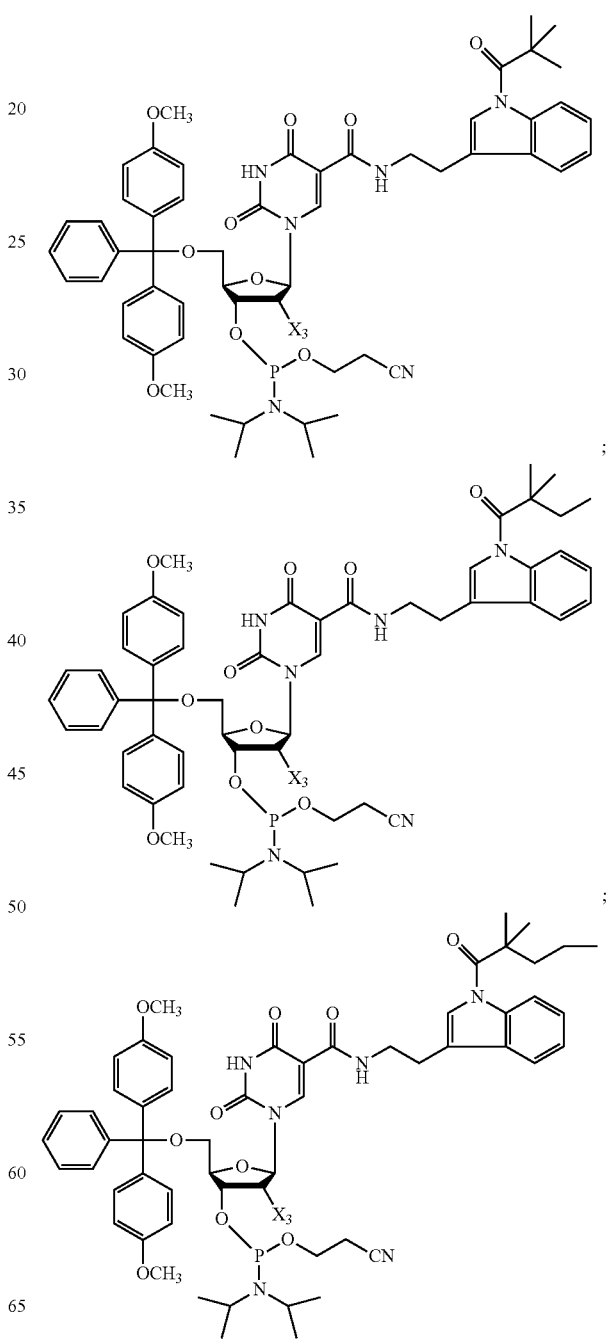

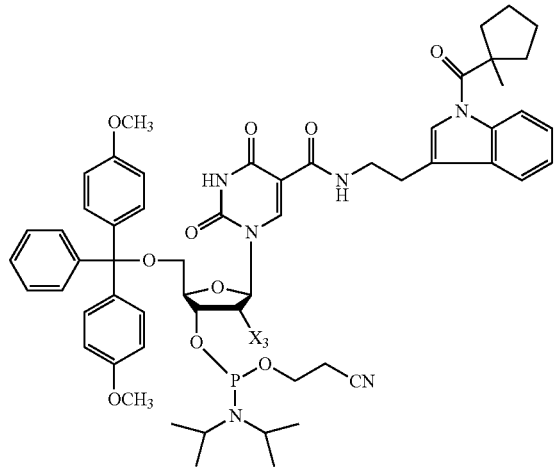

;

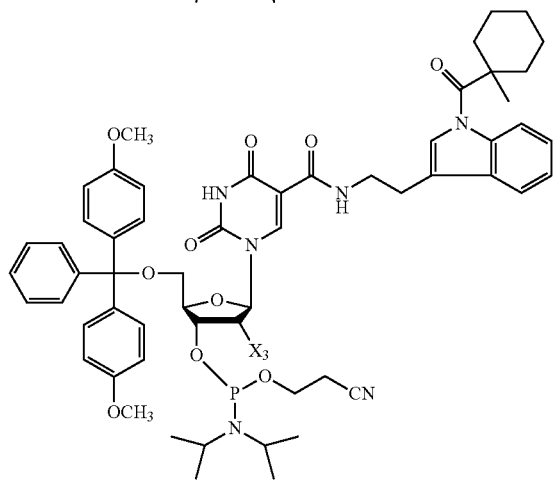

;

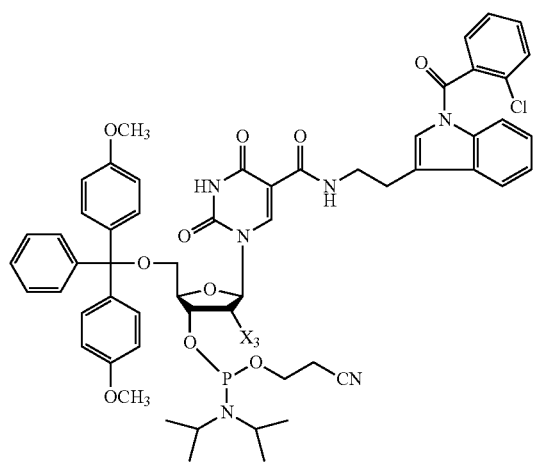

;

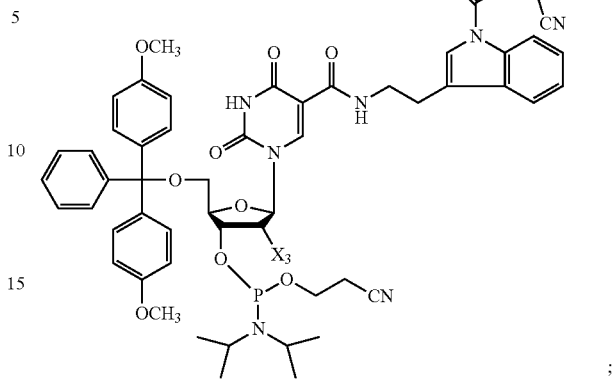

;

and salts thereof.

In some embodiments, a compound having the structure

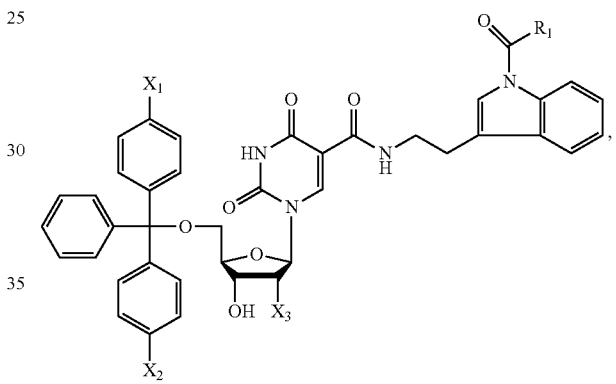

or a salt thereof, is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $X_1$ and $X_2$ are each independently selected from methoxy and hydrogen. In some embodiments, $X_3$ is selected from a methoxy, fluoro, hydrogen, and tert-butyldimethylsilyloxy.

In some embodiments, $R_1$ is tert-butyl. In some embodiments, $R_1$ is 1,1-dimethyl-propyl. In some embodiments, $R_1$ is 1,1-dimethyl-butyl; 2-chlorophenyl. In some embodiments, $R_1$ is 2-cyanophenyl. In some embodiments, $R_1$ is 1-methyl-cyclopentyl. In some embodiments, $R_1$ is 1-methyl-cyclohexyl. In some embodiments, $X_1$ and $X_2$ are methoxy. In some embodiments, $X_3$ is hydrogen. In some embodiments, $X_3$ is methoxy. In some embodiments, $X_3$ is fluoro. In some embodiments, $X_3$ is tert-butyldimethylsilyloxy.

In some embodiments, the compound is selected from:

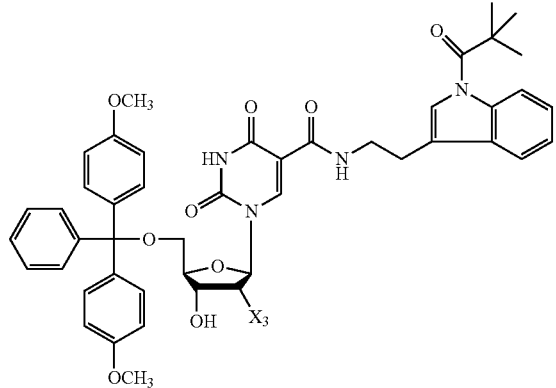

;

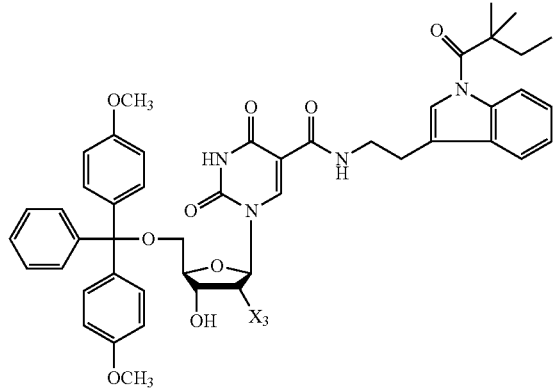

;

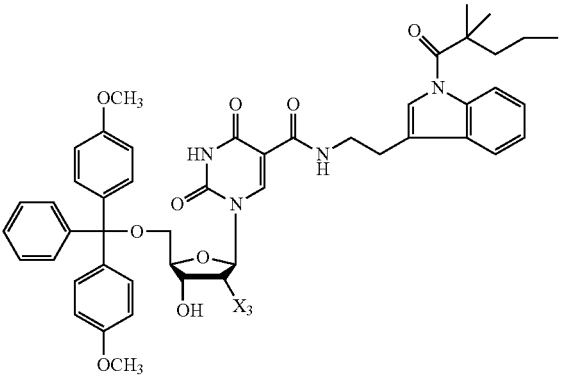

;

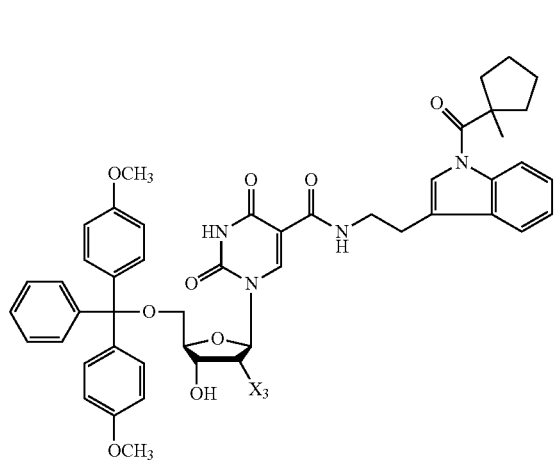

;

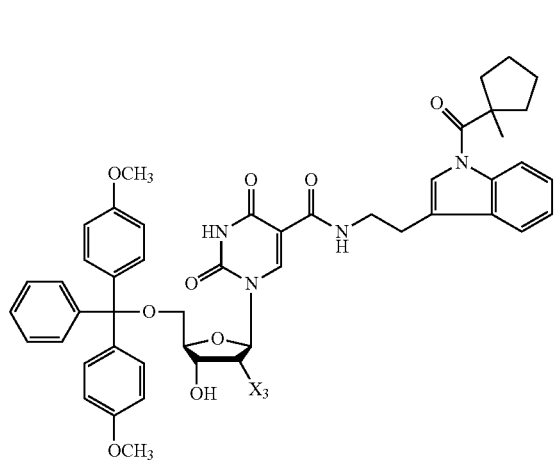

;

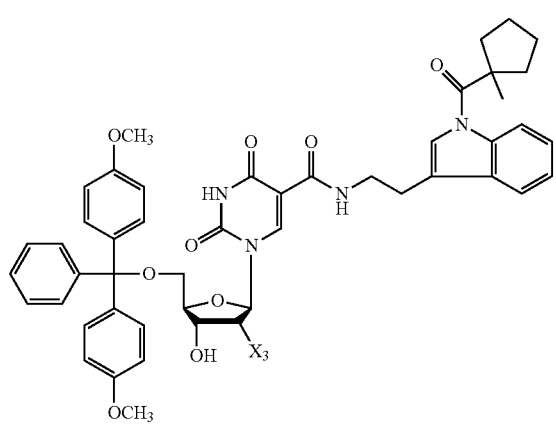

;

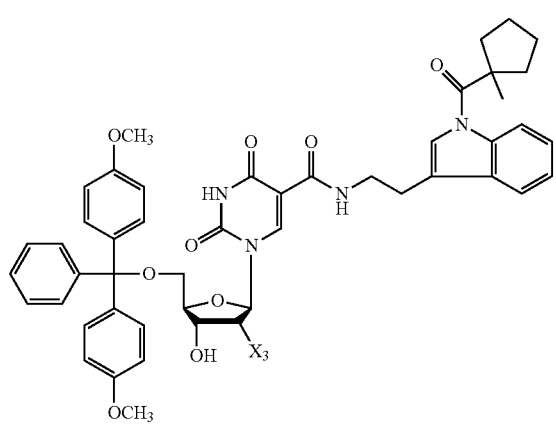

;

and salts thereof.

In some embodiments, a compound having the structure:

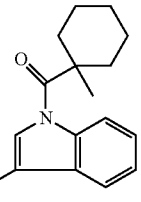

or a salt thereof, is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $R_1$ is tert-butyl. In some embodiments, $R_1$ is 1,1-dimethyl-propyl. In some embodiments, $R_1$ is 1,1-dimethyl-butyl; 2-chlorophenyl. In some embodiments, $R_1$ is 2-cyanophenyl. In some embodiments, $R_1$ is 1-methyl-cyclopentyl. In some embodiments, $R_1$ is 1-methyl-cyclohexyl.

In some embodiments, the compound has a structure selected from:

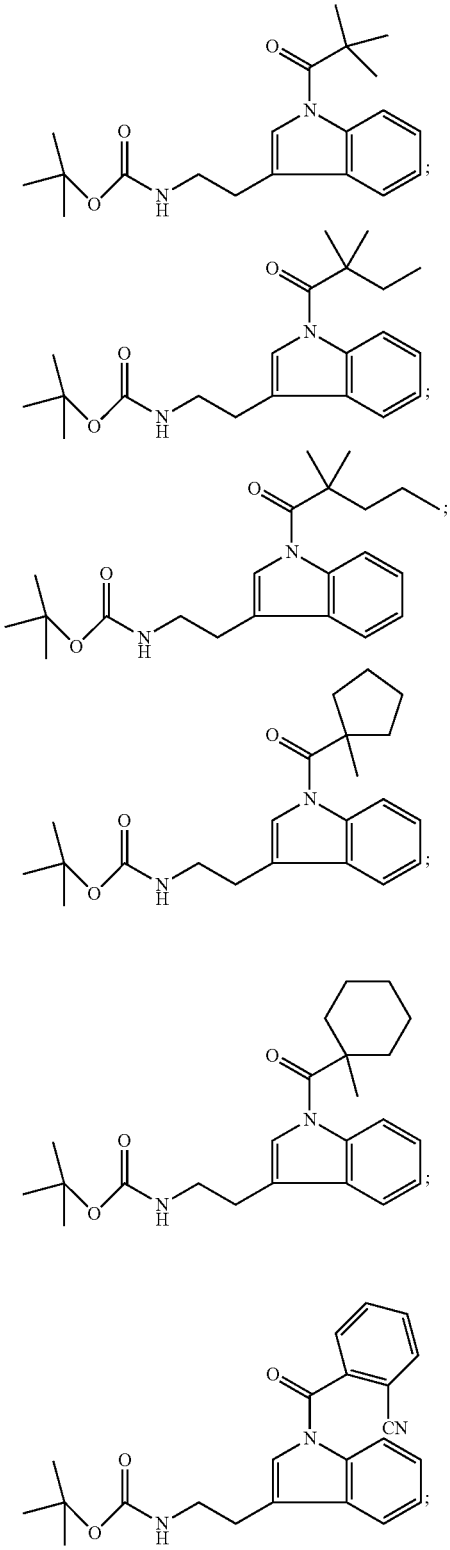

-continued

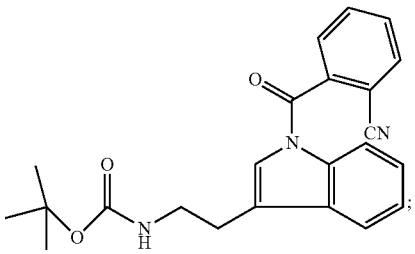

and salts thereof.

In some embodiments, a compound having the structure:

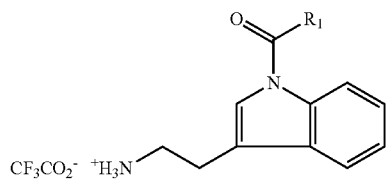

is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $R_1$ is tert-butyl. In some embodiments, $R_1$ is 1,1-dimethyl-propyl. In some embodiments, $R_1$ is 1,1-dimethyl-butyl; 2-chlorophenyl. In some embodiments, $R_1$ is 2-cyanophenyl. In some embodiments, $R_1$ is 1-methyl-cyclopentyl. In some embodiments, $R_1$ is 1-methyl-cyclohexyl.

In some embodiments, a compound has a structure selected from:

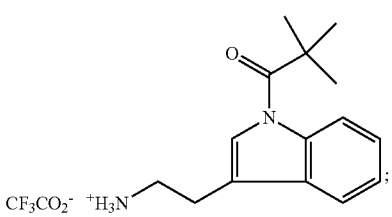

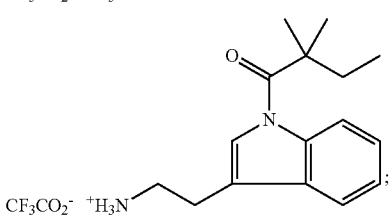

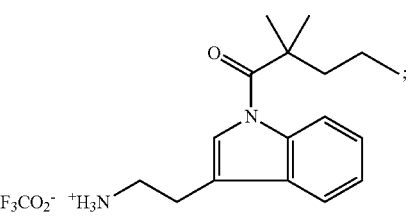

-continued

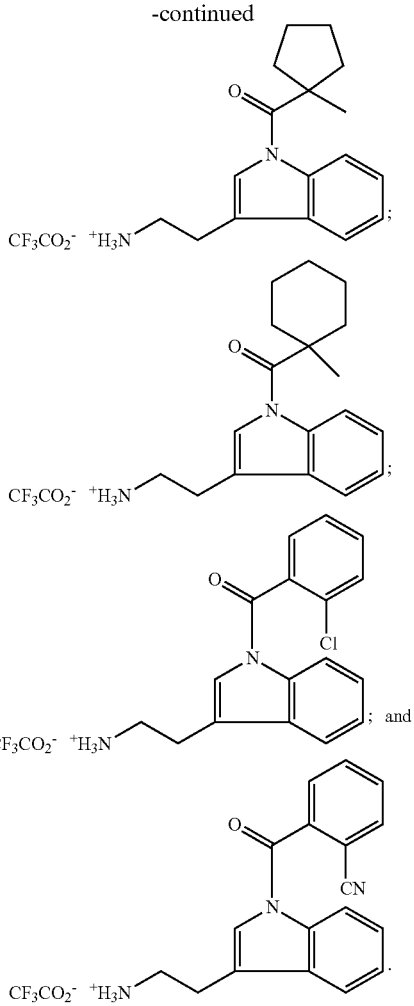

In some embodiments, methods of producing a compound having the structure:

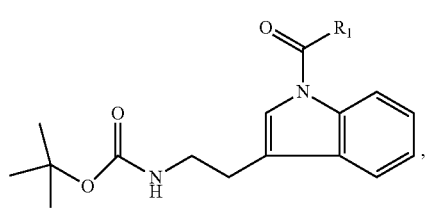

or a salt thereof, are provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $R_1$ is tert-butyl. In some embodiments, $R_1$ is 1,1-dimethyl-propyl. In some embodiments, $R_1$ is 1,1-dimethyl-butyl; 2-chlorophenyl. In some embodiments, $R_1$ is 2-cyanophenyl. In some embodiments, $R_1$ is 1-methyl-cyclopentyl. In some embodiments, $R_1$ is 1-methyl-cyclohexyl. In some embodiments, the method comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride. In some embodiments, $R_1$ is tert-butyl, and wherein the acid chloride is pivaloyl chloride. In some embodiments, $R_1$ is 1,1-dimethyl-propyl and the acid chloride is 2,2-dimethylbutyroyl chloride. In some embodiments, $R_1$ is 1,1-dimethyl-butyl and the acid chloride is 2,2-dimethylvaleroyl chloride. In some embodiments, $R_1$ is 2-chlorophenyl and the acid chloride is 2-chlorobenzoyl chloride. In some embodiments, $R_1$ is 2-cyanophenyl and the acid chloride is 2-cyanobenzoyl chloride. In some embodiments, $R_1$ is 1-methyl-cyclopentyl and the acid chloride is 1-methylcyclopentane-1-carbonyl chloride. In some embodiments, $R_1$ is 1-methyl-cyclohexyl and the acid chloride is 1-methylcyclohexane-1-carbonyl chloride.

In some embodiments, the method produces a compound selected from

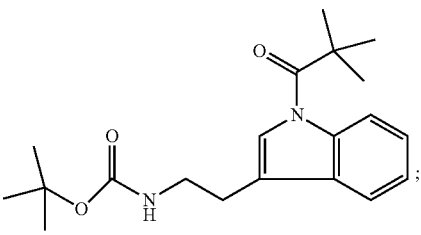

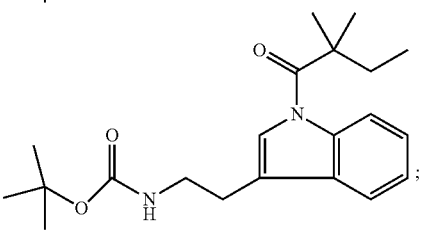

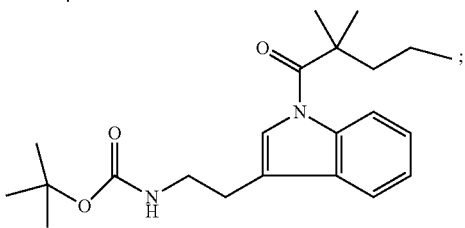

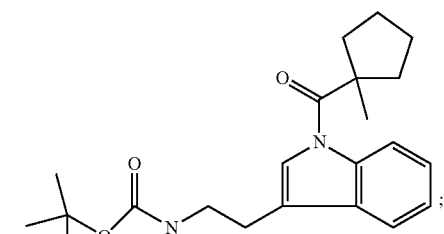

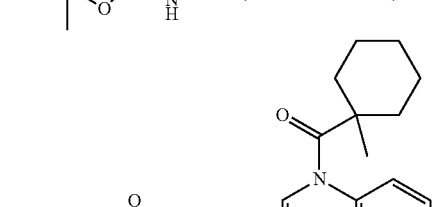

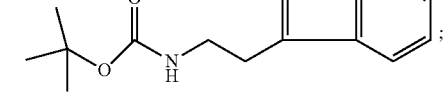

-continued

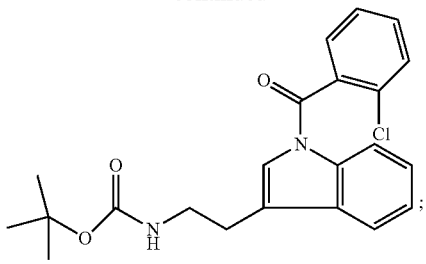

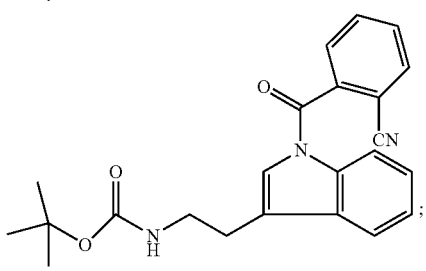

and salts thereof.

In some embodiments, a method of producing a compound having the structure:

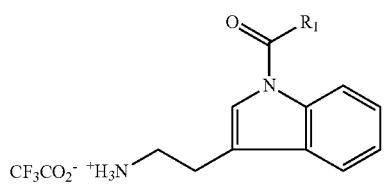

is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, the method comprises reacting the compound

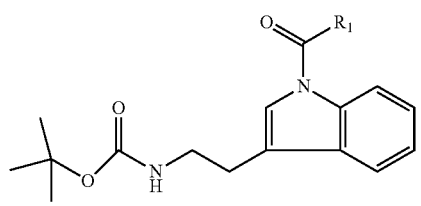

with trifluoroacetic acid.

In some embodiments, the method produces a compound selected from:

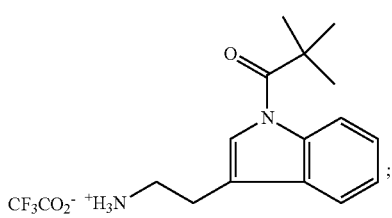

-continued

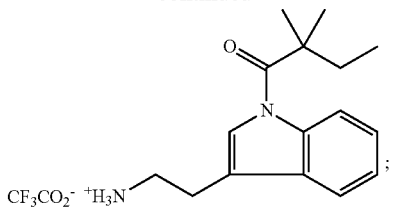

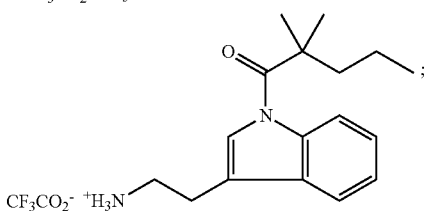

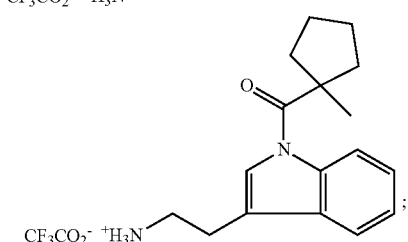

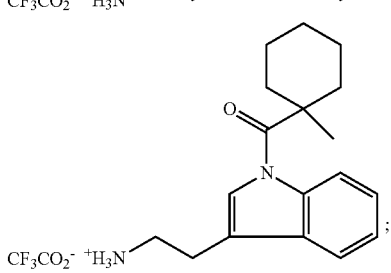

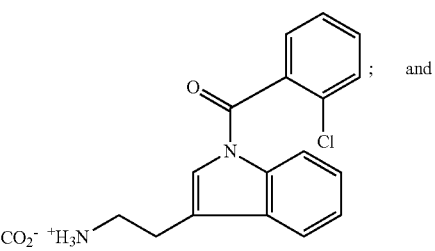 and

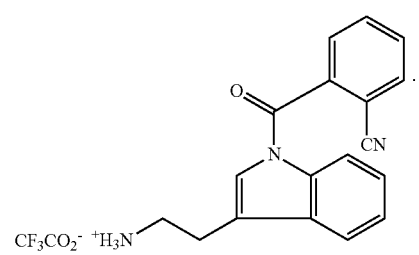

In some embodiments, the method further comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

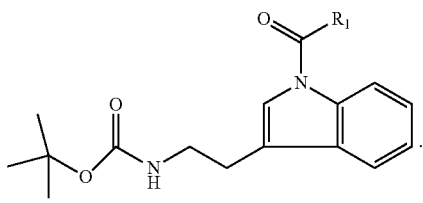

In some embodiments, a method of producing a compound having the structure:

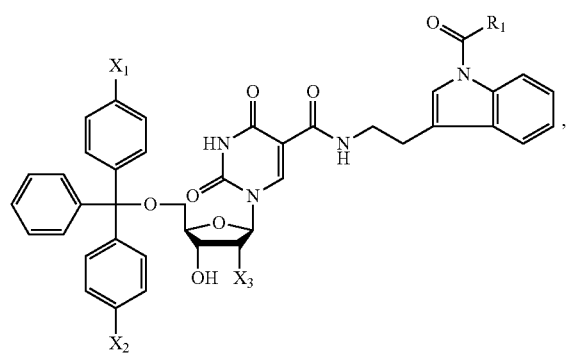

or a salt thereof, is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $X_1$ and $X_2$ are each independently selected from methoxy and hydrogen. In some embodiments, $X_3$ is selected from a methoxy, fluoro, hydrogen, and tert-butyldimethylsilyloxy. In some embodiments, the method comprising reacting the compound

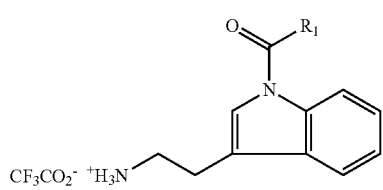

with 5'-O-DMT-5-(2,2,2-trifluoroethyoxy-carbonyl)-2'-deoxyuridine (TFEdU).

In some embodiments, the method produces a compound selected from:

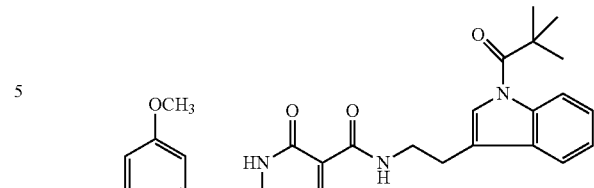

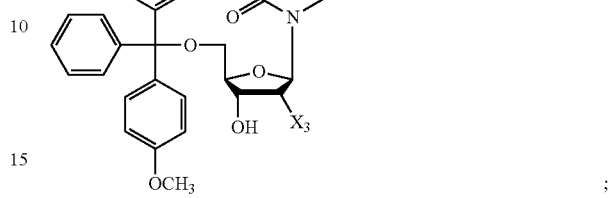

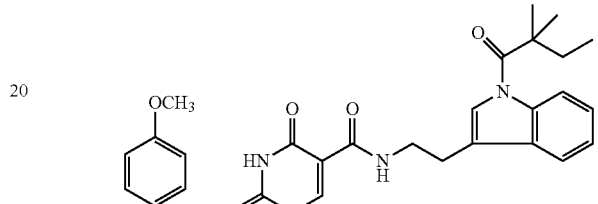

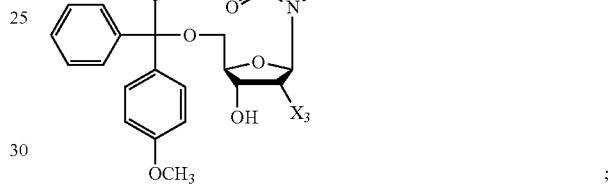

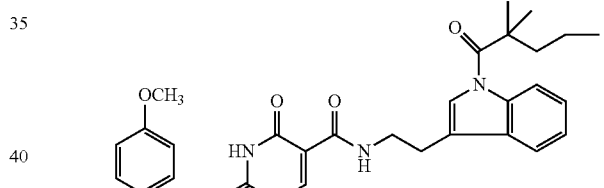

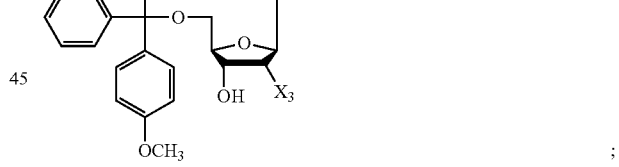

-continued

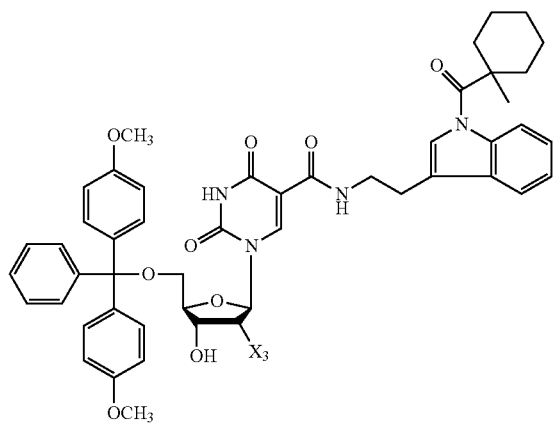

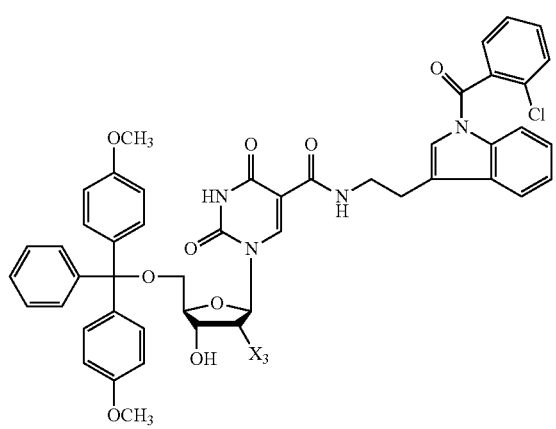

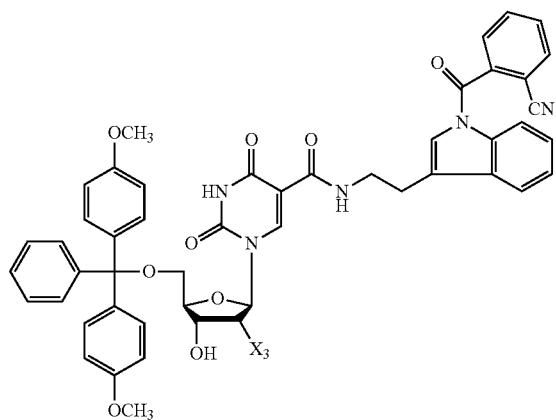

and salts thereof.

In some embodiments, the method further comprises reacting the compound

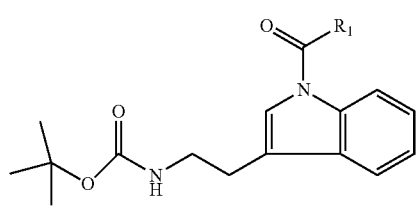

with trifluoroacetic acid to form the compound

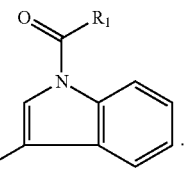

In some embodiments, the method further comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

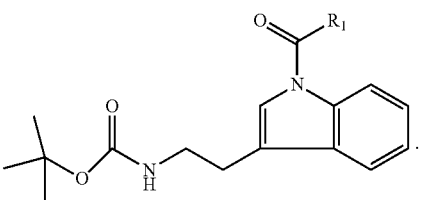

In some embodiments, a method of producing a compound having the structure:

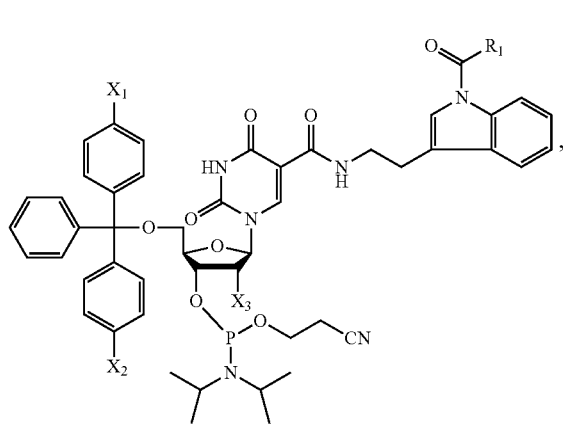

or a salt thereof, is provided. In some embodiments, $R_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, $X_1$ and $X_2$ are each independently selected from methoxy and hydrogen. In some embodiments, $X_3$ is selected from a methoxy, fluoro, hydrogen, and tert-butyldimethylsilyloxy. In some embodiments, the method comprises reacting the compound

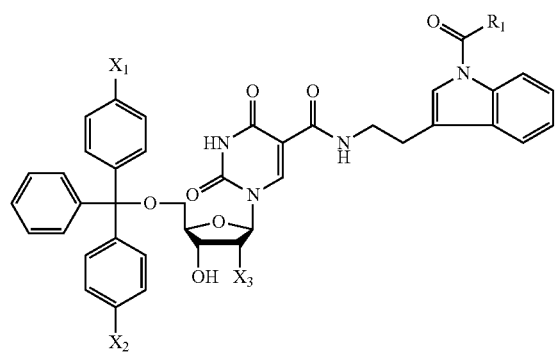

with 2-cyanoethyl-N,N,N',N'-tetraisopropylphosphor-amidite.

In some embodiments, the method comprises reacting the compound

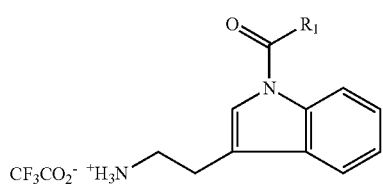

with 5'-O-DMT-5-(2,2,2-trifluoroethyoxy-carbonyl)-2'-deoxyuridine (TFEdU) to form the compound

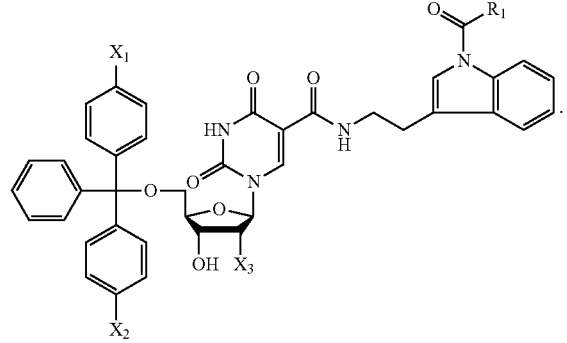

In some embodiments, the method comprises reacting the compound

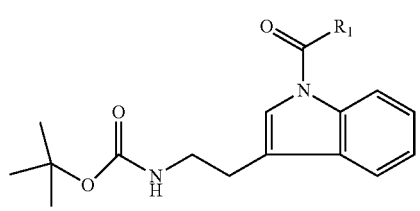

with trifluoroacetic acid to form the compound

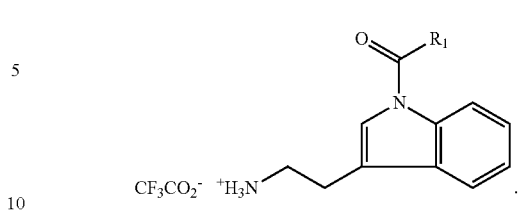

In some embodiments, the method comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

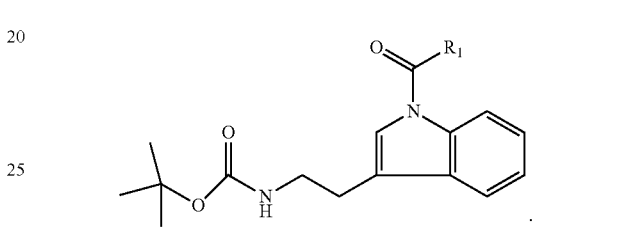

In some embodiments, the method produces a compound selected from:

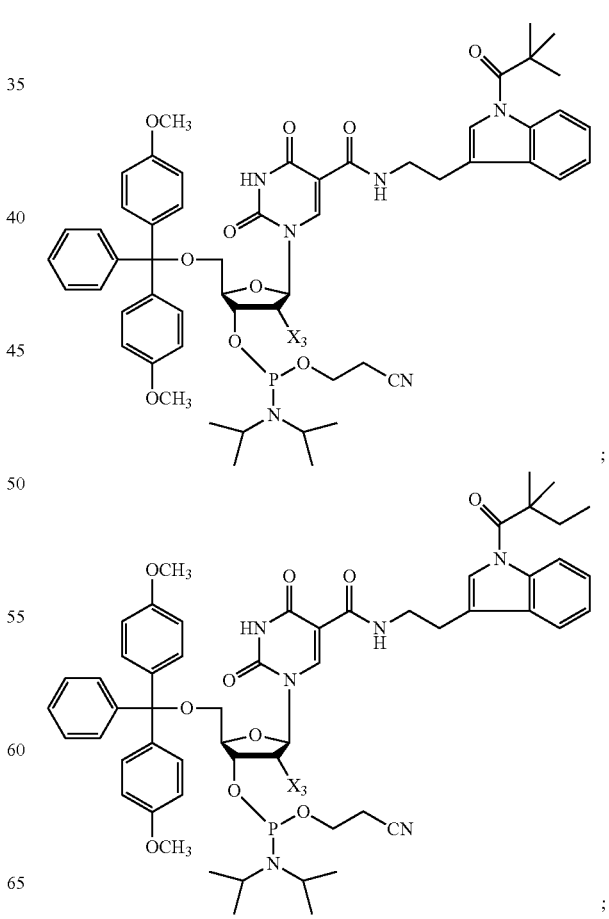

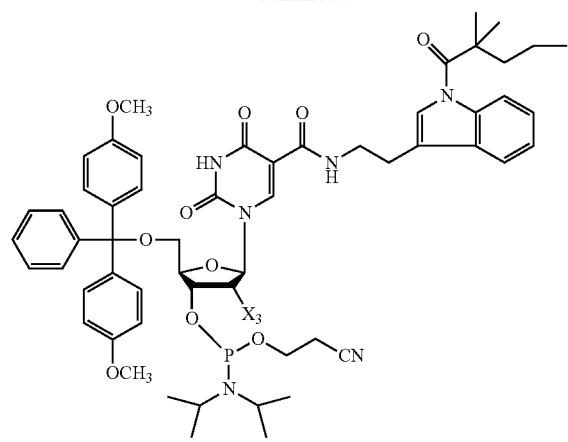
;
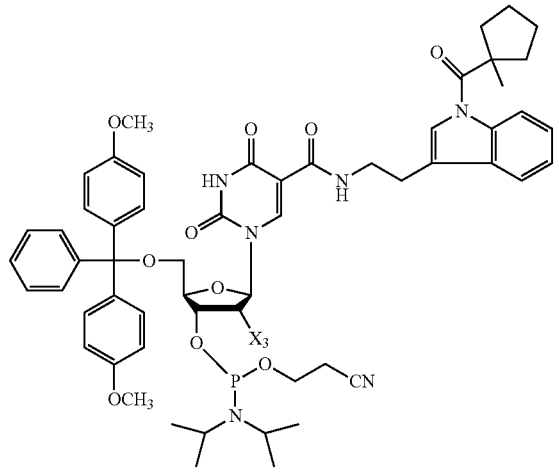
;
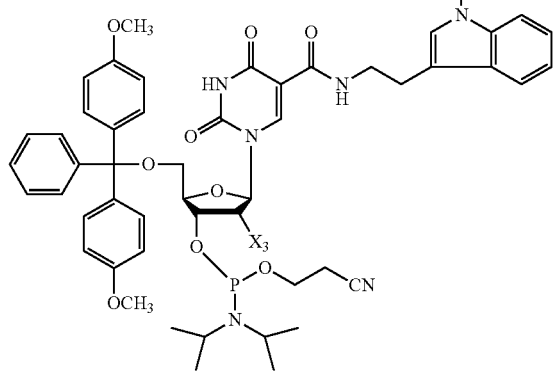
;
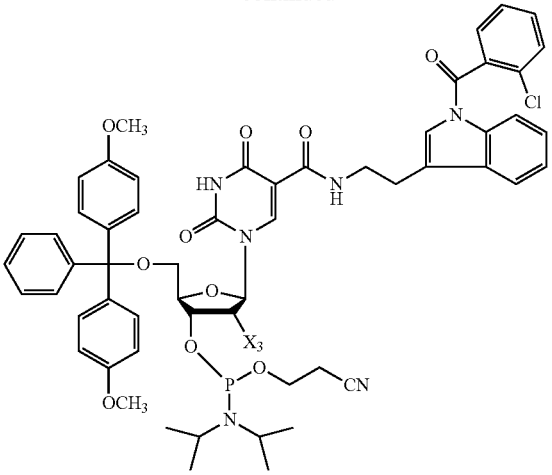
;
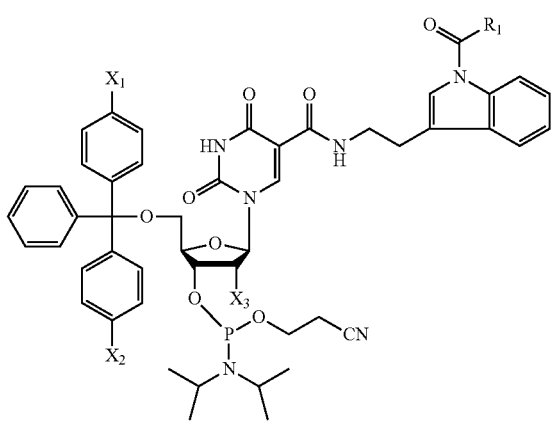
;
and salts thereof.
In some embodiments, a method of producing a compound having the structure:
or a salt thereof, is provided, wherein,
R₁ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl;
X₁ and X₂ are each independently selected from methoxy and hydrogen;

$X_3$ is selected from a methoxy, fluoro, hydrogen, and tert-butyldimethylsilyloxy; comprising the steps of:

a) reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

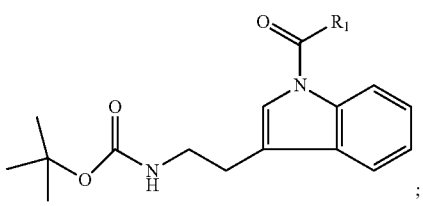

b) reacting the compound

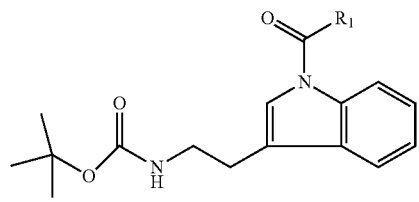

with trifluoroacetic acid to form the compound

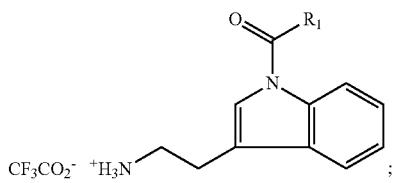

c) reacting the compound

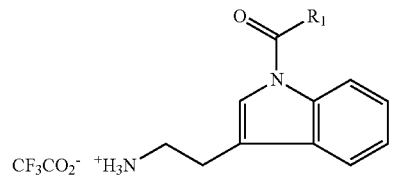

with 5'-O-DMT-5-(2,2,2-trifluoroethyoxy-carbonyl)-2'-deoxyuridine (TFEdU) to form the compound

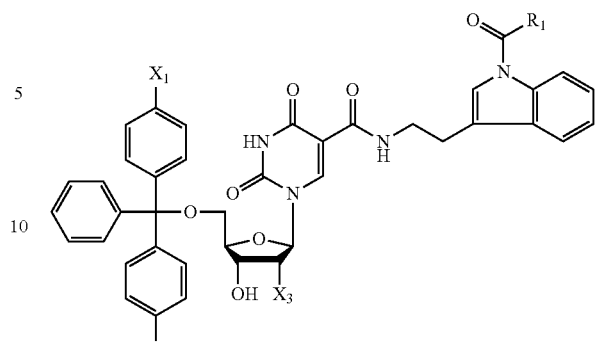

and d) reacting the compound

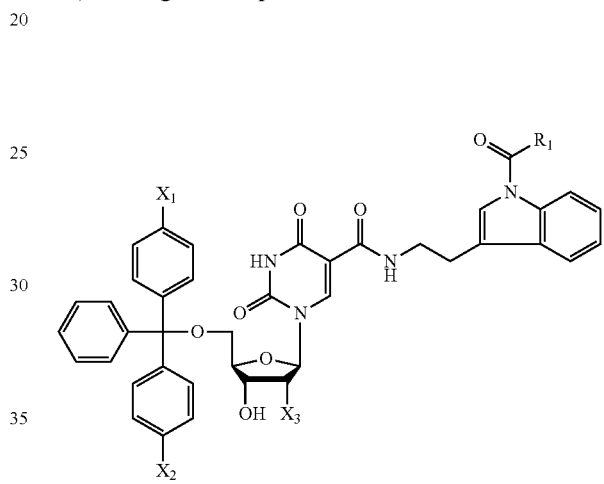

with 2-cyanoethyl-N,N,N',N'-tetraisopropylphosphor-amidite.

In some embodiments, the method produces a compound selected from:

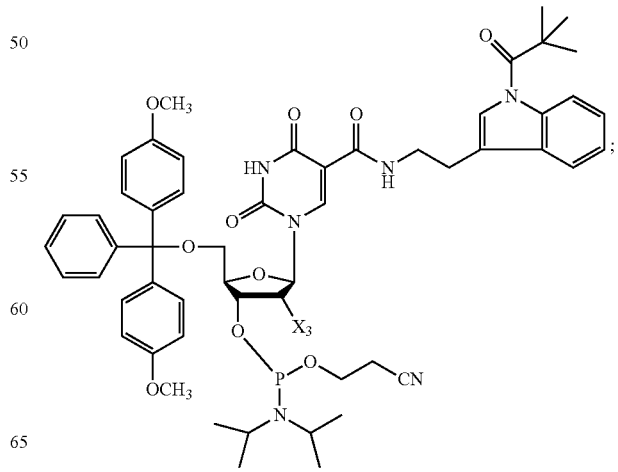

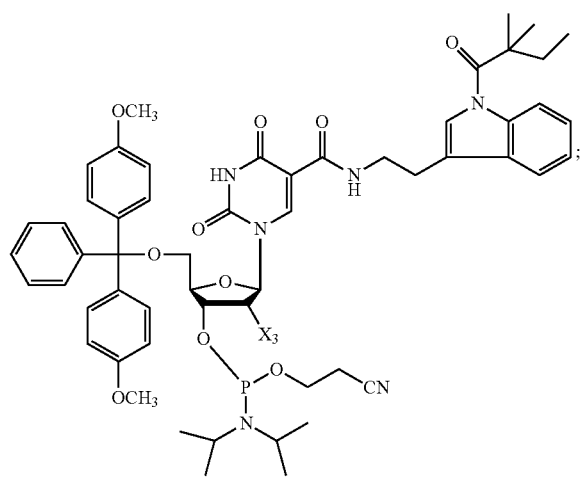
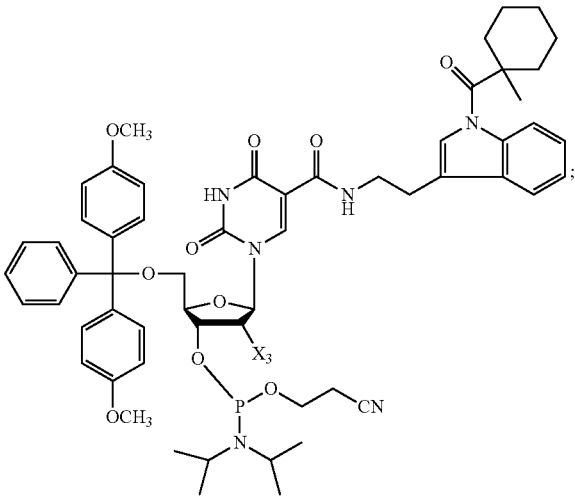
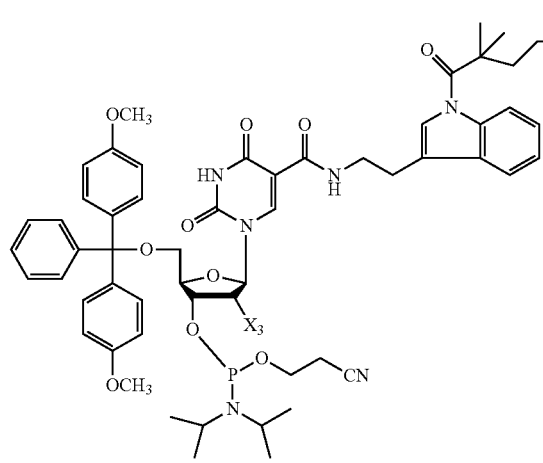
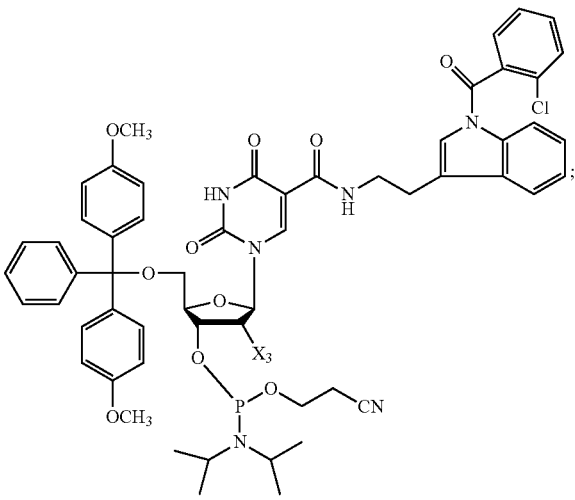
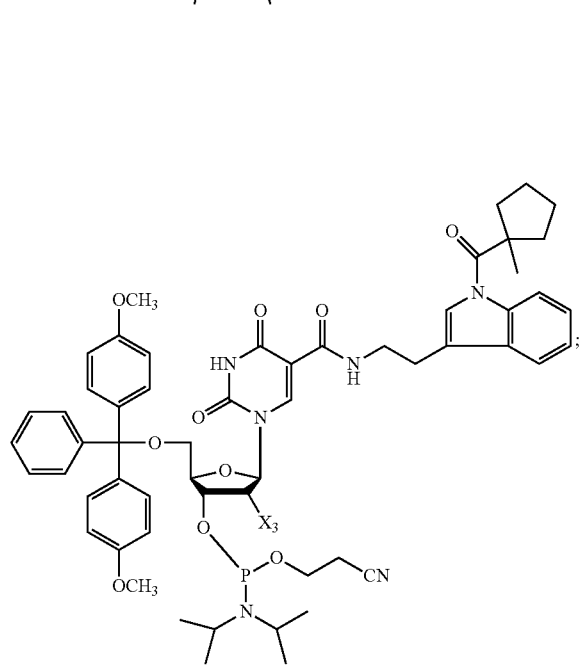
and salts thereof.
In some embodiments, oligonucleotides are provided, comprising at least one protected TrpU nucleotide, wherein at least one protected TrpU nucleotide in the oligonucleotide has the structure:

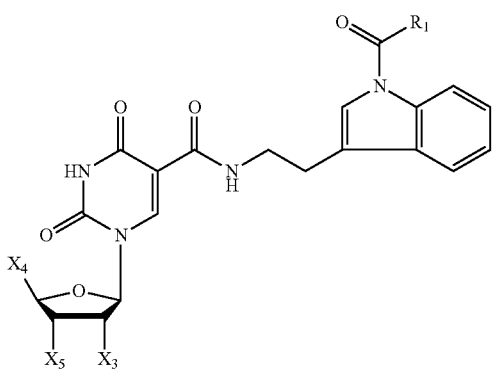

In some embodiments, R$_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, X$_3$ is selected from a methoxy, fluoro, hydrogen, and tert-butyldimethylsilyloxy. In some embodiments, X$_4$ is selected from OH, —OR, —SR, and —Z—P(Z')(Z")O—R, wherein Z, Z', and Z" are each independently selected from —O and S, and R is an adjacent nucleotide in the oligonucleotide. In some embodiments, X$_5$ is selected from —O-ss, —OR, —SR, and —Z—P(Z')(Z")O—R, wherein ss is a solid support, Z, Z', and Z" are each independently selected from O and S, and R is an adjacent nucleotide in the oligonucleotide. In some embodiments, the solid support is controlled-pore glass (CPG). In some embodiments, Z' is S and Z" is O. In some embodiments, Z' and Z" are O.

In some embodiments, a method of producing an oligonucleotide comprising at least one TrpU nucleotide is provided, comprising incorporating at least one nucleotide having the structure:

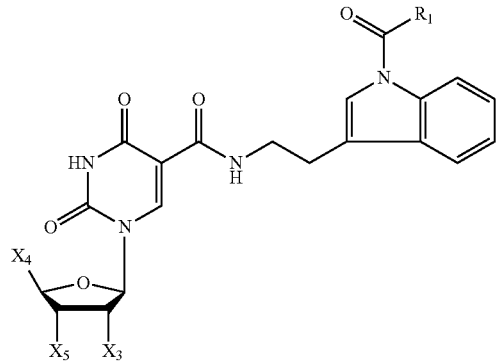

into a nucleotide sequence on a solid support; and removing the

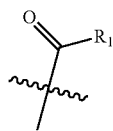

protecting group from the at least one TrpU nucleotide incorporated into the oligonucleotide. In some embodiments, R$_1$ is selected from tert-butyl, 1,1-dimethyl-propyl; 1,1-dimethyl-butyl; 2-chlorophenyl; 2-cyanophenyl; 1-methyl-cyclopentyl; and 1-methyl-cyclohexyl. In some embodiments, X$_3$ is selected from a methoxy, fluoro, hydrogen, and tert-butyldimethylsilyloxy. In some embodiments, X$_4$ is selected from OH, —OR, —SR, and —Z—P(Z')(Z") O—R, wherein Z, Z', and Z" are each independently selected from O and S, and R is an adjacent nucleotide in the oligonucleotide. In some embodiments, X$_5$ is selected from —O-ss, —OR, —SR, and —Z—P(Z')(Z")O—R, wherein ss is a solid support, Z, Z', and Z" are each independently selected from O and S, and R is an adjacent nucleotide in the oligonucleotide. In some embodiments, the solid support is controlled-pore glass (CPG). In some embodiments, Z' is S and Z" is O. In some embodiments, Z' and Z" are O.

DETAILED DESCRIPTION

Figure 1:
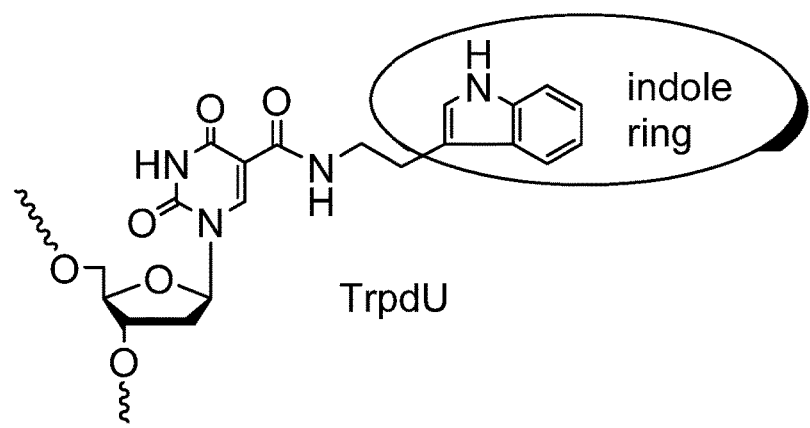
FIG. 1. Structure of TrpdU.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," " an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" 60 mean±20% of the indicated range, value, or structure, unless otherwise indicated. As used herein, the terms "include" and "comprise" are open ended and are used synonymously.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, the term "TrpU" is used to generally refer to uridylyl nucleotides comprising a 5-position N-(3-indole-2-ethyl)-carboxamide functional group. Use of the term "TrpU" is not intended to be limiting with regard to the 2' position of the ribose, and the term should be construed to include, but not be limited to, nucleotides comprising —H, —OH, —OMe, or —F at the 2'-position, unless a particular 2' moiety is indicated. The term "TrpdU" typically refers to the TrpU nucleotide comprising a 2'-H.

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the term "at least one nucleotide" when referring to modifications of a nucleic acid, refers to one, several, or all nucleotides in the nucleic acid, indicating that any or all occurrences of any or all of A, C, T, G or U in a nucleic acid may be modified or not.

As used herein, a "phorphoramidite" is a nucleotide comprising a

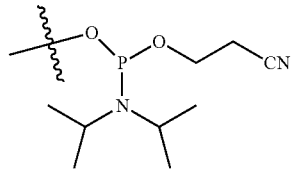 [SMILES: *OP(OCCC#N)N(C(C)C)C(C)C]

group attached to the 3' carbon of the ribose, or an equivalent position on another sugar moiety. In some embodiments, a phosphoramidite comprises a protecting group on the 5'-OH of the ribose, such as a trityl protecting group, for example, a dimethoxytrityl protecting group.

As used herein, "solid phase synthesis" refers to solid-phase oligonucleotide synthesis using phosphoramidite chemistry, unless specifically indicated otherwise.

Compounds

The present disclosure provides the compounds shown in Table A, as well as salts thereof, and methods of making and using the compounds.

TABLE A

Compounds of the disclosure

| | Compound Name | Structure |
|---|---|---|
| 1 | Piv-TrpU CEP | 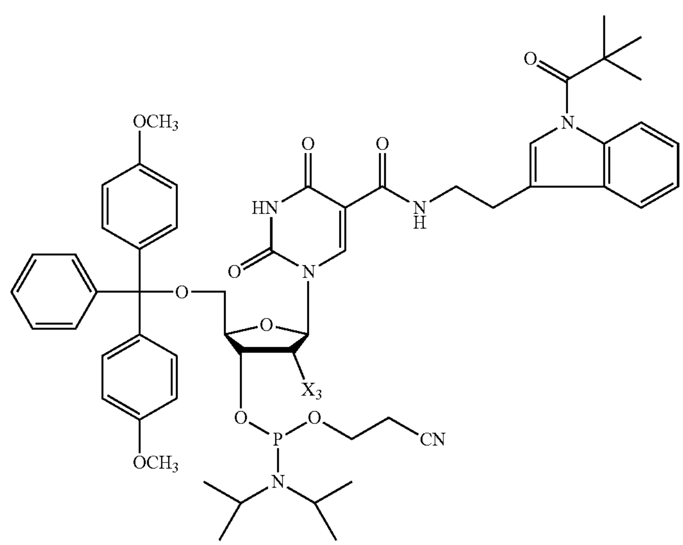 |

TABLE A-continued
Compounds of the disclosure
| Compound Name | Structure |
|---|---|
| 2 Dmb-TrpU CEP | 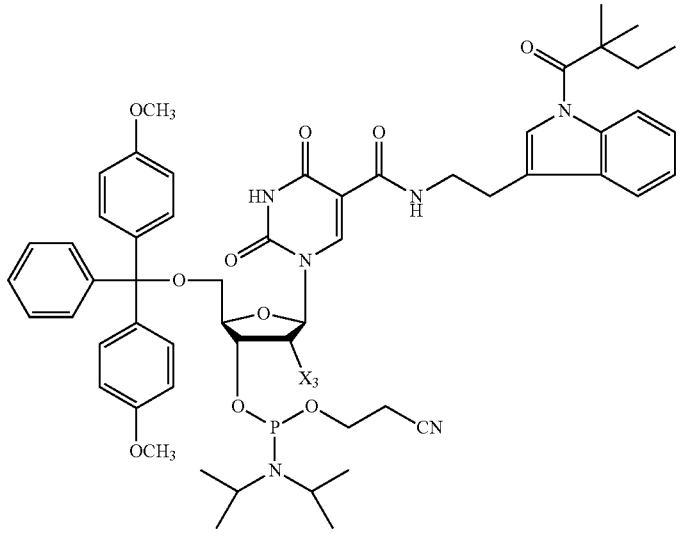 |
| 3 Dmv-TrpU CEP | 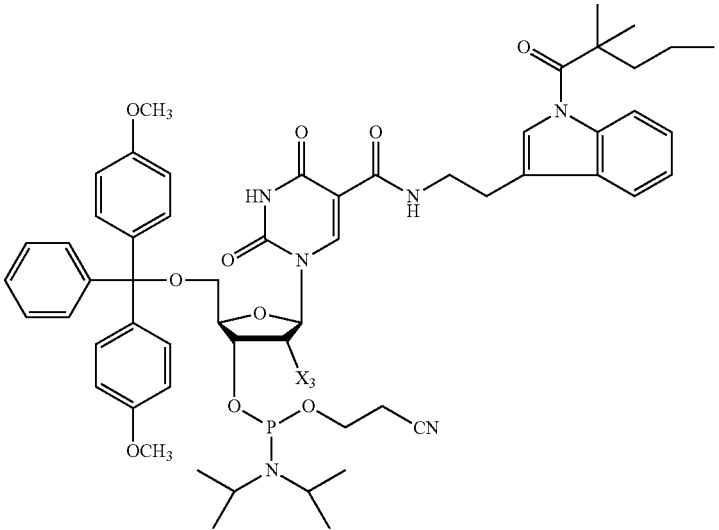 |

TABLE A-continued
Compounds of the disclosure
| Compound Name | Structure |
|---|---|
| 4  Mcp-TrpU CEP | 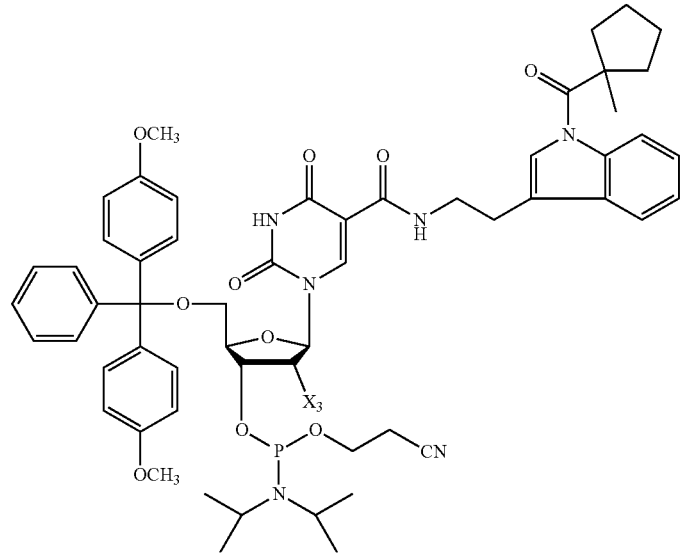 |
| 5  Mch-TrpU CEP | 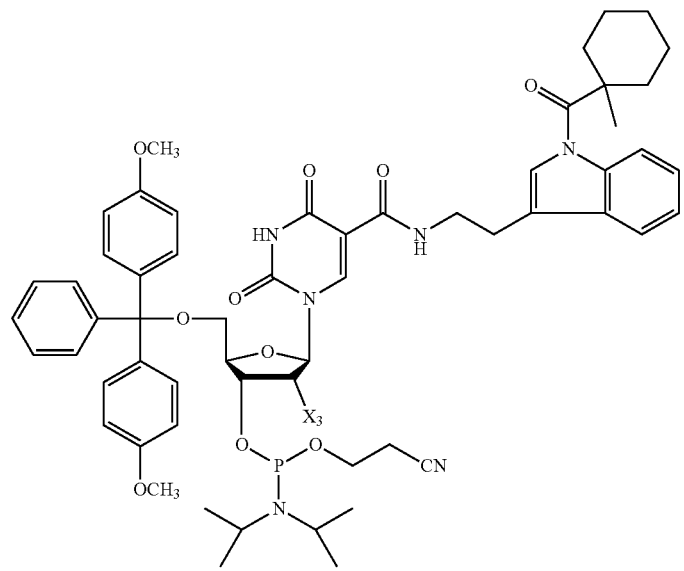 |

TABLE A-continued
Compounds of the disclosure
| Compound Name | | Structure |
|---|---|---|
| 6 | Clp-TrpU CEP | 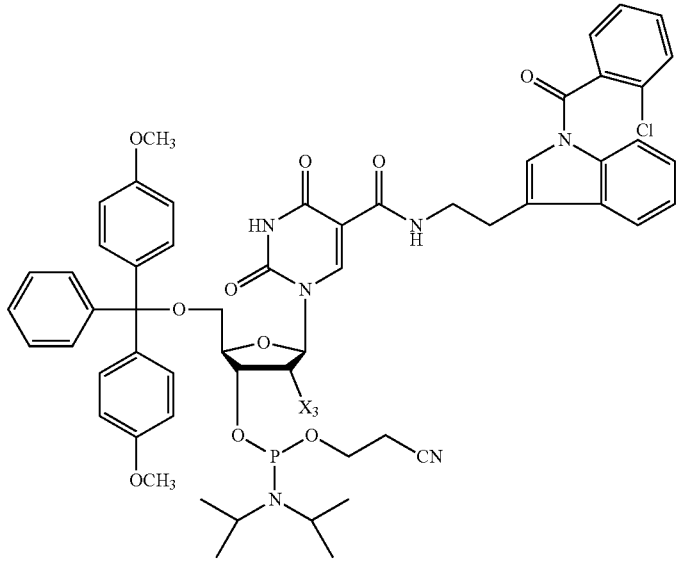 |
| 7 | Cyp-TrpU CEP | 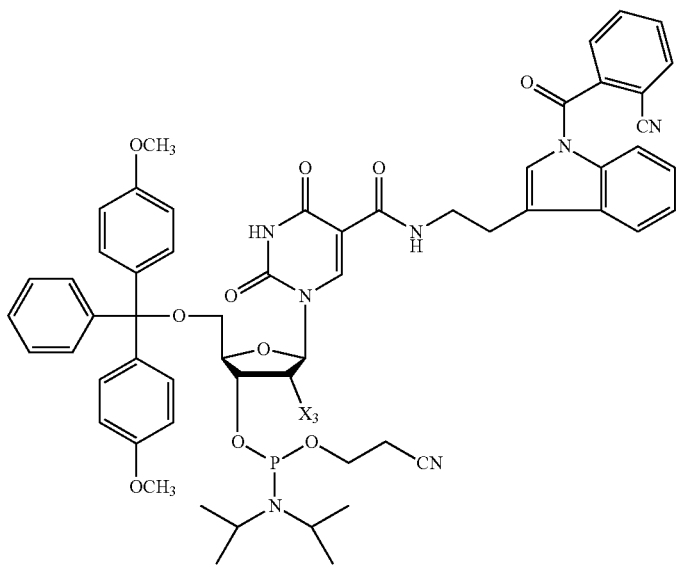 |

TABLE A-continued

Compounds of the disclosure

| Compound | Name | Structure |
|---|---|---|
| 8 | DMT-Piv-TrpU | |
| 8 | DMT-Dmb-TrpU | |
| 10 | DMT-Dmv-TrpU | 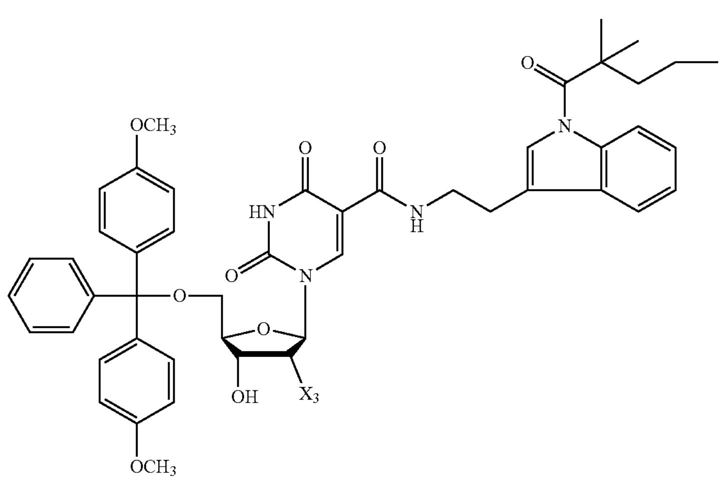 |

TABLE A-continued

Compounds of the disclosure

| Compound Name | | Structure |
|---|---|---|
| 11 | DMT-Mcp-TrpU | |
| 12 | DMT-Mch-TrpU | |
| 13 | DMT-Clp-TrpU | |

TABLE A-continued

Compounds of the disclosure

| Compound | Name | Structure |
|---|---|---|
| 14 | DMT-Cyp-TrpU | 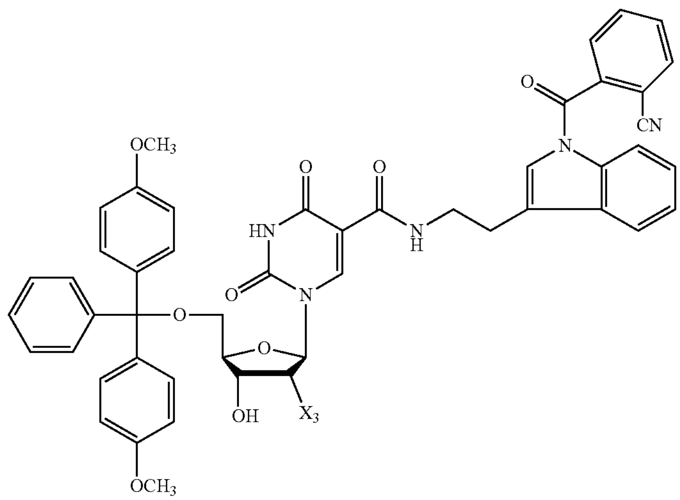 |
| 15 | Piv-BOC-Trp | 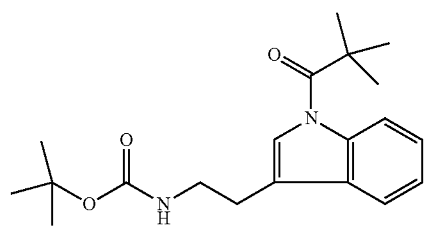 [SMILES: CC(C)(C)OC(=O)NCCc1cn(C(=O)C(C)(C)C)c2ccccc12] |
| 16 | Dmb-BOC-Trp | 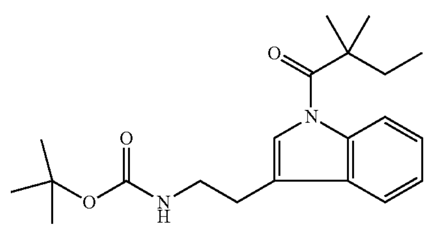 [SMILES: CCC(C)(C)C(=O)n1cc(CCNC(=O)OC(C)(C)C)c2ccccc21] |
| 17 | Dmv-BOC-Trp | 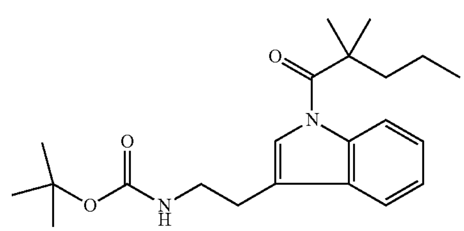 [SMILES: CCCC(C)(C)C(=O)n1cc(CCNC(=O)OC(C)(C)C)c2ccccc21] |
| 18 | Mcp-BOC-Trp | 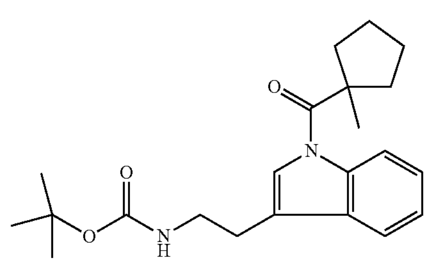 [SMILES: CC(C)(C)OC(=O)NCCc1cn(C(=O)C2(C)CCCC2)c2ccccc12] |

TABLE A-continued

Compounds of the disclosure

| Compound Name | | Structure |
|---|---|---|
| 19 | Mch-BOC-Trp | 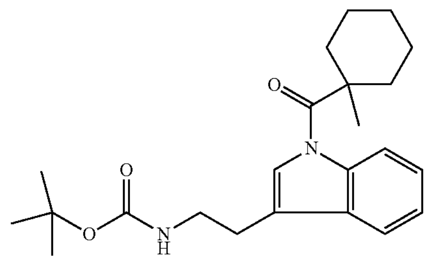 [SMILES: CC(C)(C)OC(=O)NCCc1cn(C(=O)C2(C)CCCCC2)c2ccccc12] |
| 20 | Clp-BOC-Trp | 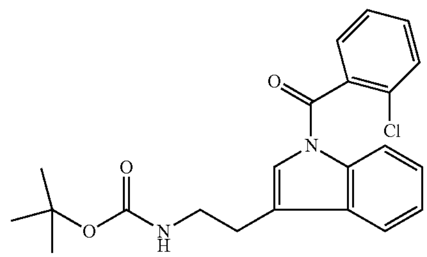 [SMILES: CC(C)(C)OC(=O)NCCc1cn(C(=O)c2ccccc2Cl)c2ccccc12] |
| 21 | Cyp-BOC-Trp | 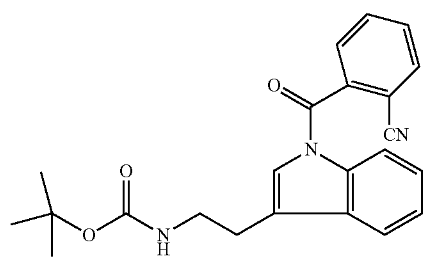 [SMILES: CC(C)(C)OC(=O)NCCc1cn(C(=O)c2ccccc2C#N)c2ccccc12] |
| 22 | Piv-Trp•TFA | 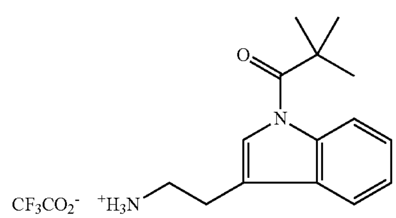 [SMILES: "CF3CO2-" ; CC(C)(C)C(=O)n1cc(CC[NH3+])c2ccccc21] |
| 23 | Dmb-Trp•TFA | 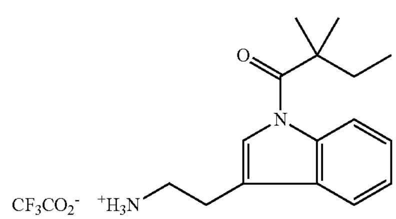 [SMILES: "CF3CO2-" ; CCC(C)(C)C(=O)n1cc(CC[NH3+])c2ccccc21] |
| 24 | Dmv-Trp•TFA | 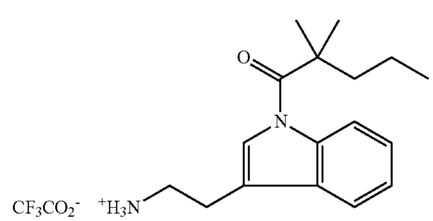 [SMILES: "CF3CO2-" ; CCCC(C)(C)C(=O)n1cc(CC[NH3+])c2ccccc21] |

TABLE A-continued

Compounds of the disclosure

| Compound Name | | Structure |
|---|---|---|
| 25 | Mcp-Trp•TFA | (1-methylcyclopentyl carbonyl indole with tryptamine, CF$_3$CO$_2^-$ $^+$H$_3$N) |
| 26 | Mch-Trp•TFA | (1-methylcyclohexyl carbonyl indole with tryptamine, CF$_3$CO$_2^-$ $^+$H$_3$N) |
| 27 | Clp-Trp•TFA | (2-chlorobenzoyl indole with tryptamine, CF$_3$CO$_2^-$ $^+$H$_3$N) |
| 28 | Cyp-Trp•TFA | (2-cyanobenzoyl indole with tryptamine, CF$_3$CO$_2^-$ $^+$H$_3$N) |

$X_3$ in the structures in Table A may, in some embodiments, be selected from methoxy, fluoro, hydrogen, and tert-butyldimethylsilyloxy. In some embodiments, compounds 1 to 7 in Table A may be used in solid-phase oligonucleotide synthesis to produce oligonucleotides comprising one or more TrpU nucleotides. Also provided herein are compounds comprising a structure selected from compounds 8 to 14, wherein the 3' carbon of the ribose is linked to a solid phase, such as controlled-pore glass, through a linker moiety. In some embodiments, the 3' carbon of the ribose is linked to a solid phase through a linker moiety selected from succinate, diglycolate, and alkylamino.

The compounds in Table A may be synthesized, in some embodiments, using the methods described herein, such as in the Examples herein.

Salts

It may be convenient or desirable to prepare, purify, and/or handle a corresponding salt of the compound.

For example, if the compound is anionic, or has a functional group which may be anionic (e.g., —COOH may be —COO—), then a salt may be formed with a suitable cation. Examples of suitable inorganic cations include, but are not limited to, alkali metal ions such as Na$^+$ and K$^+$, alkaline earth cations such as Ca$^{2-}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^{X+}$, NH$_2$R$^X_2{}^+$, NHR$^X_3{}^+$, NR$^X_4{}^+$. Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Modified Oligonucleotides

As used herein, the terms "modify," "modified," "modification," and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. Additional modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers.

Polynucleotides can also contain analogous forms of ribose or deoxyribose sugars that are generally known in the art, including 2'-O-methyl, 2'-O—CH$_2$CH$_2$OCH$_3$, 2'-fluoro, 2'-NH$_2$ or 2'-azido, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted herein, one or more phosphodiester linkages may be replaced by alternative linking groups. These alternative linking groups include embodiments wherein phosphate is replaced by P(O)S ("thioate"), P(S)S ("dithioate"), (O)NR$^X$$_2$ ("amidate"), P(O)R$^X$, P(O)OR$^{Xi}$, CO or CH$_2$ ("formacetal"), in which each R$^X$ or R$^{Xi}$ are independently H or substituted or unsubstituted alkyl (C1-C20) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Polynucleotides can also contain analogous forms of carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside.

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

Preparation of Oligonucleotides

The automated synthesis of oligodeoxynucleosides is routine practice in many laboratories (see, e.g., Matteucci, M. D. and Caruthers, M. H., (1990) J. Am. Chem. Soc., 103:3185-3191, the contents of which are hereby incorporated by reference in their entirety). Synthesis of oligoribonucleosides is also well known (see e.g. Scaringe, S. A., et al., (1990) Nucleic Acids Res. 18:5433-5441, the contents of which are hereby incorporated by reference in their entirety). As noted herein, the phosphoramidites are useful for incorporation of the modified nucleoside into an oligonucleotide by chemical synthesis, and the triphosphates are useful for incorporation of the modified nucleoside into an oligonucleotide by enzymatic synthesis. (See e.g., Vaught, J. D. et al. (2004) J. Am. Chem. Soc., 126:11231-11237; Vaught, J. V., et al. (2010) *J. Am. Chem. Soc.* 132, 4141-4151; Gait, M. J. "Oligonucleotide Synthesis a practical approach" (1984) IRL Press (Oxford, UK); Herdewijn, P. "Oligonucleotide Synthesis" (2005) (Humana Press, Totowa, N.J. (each of which is incorporated herein by reference in its entirety).

In some embodiments, the compounds provided herein, and in particular, compounds 1 to 7 of Table A, may be used in standard phosphoramidite oligonucleotide synthesis methods, including automated methods using commercially available synthesizers. Following synthesis, the protecting group on the TrpU nucleotide is removed through standard deprotection methods, such as tBuNH$_2$/MeOH/H$_2$O and MeNH$_2$ (gas).

In some embodiments, use of the compounds provided herein, such as compounds 1 to 7 of table A, in oligonucleotide synthesis improves the yield of desired oligonucleotide product. For example, as described in Example 4, use of Piv-TrpdU CEP in place of unprotected TrpdU CEP improved the yield of a 51 mer oligonucleotide comprising 13 TrpdU nucleotides by about 1.7-fold. See Table 10. For longer oligonucleotides, the yield may be increased by 2-fold or more. See Table 11.

EXAMPLES

The following examples are presented in order to more fully illustrate some embodiments of the invention. They should, in no way be construed, however, as limiting the broad scope of the invention. Those of ordinary skill in the art can readily adopt the underlying principles of this discovery to design various compounds without departing from the spirit of the current invention.

Example 1

Investigation of Protecting Groups for Tryptamine

Figure 2:
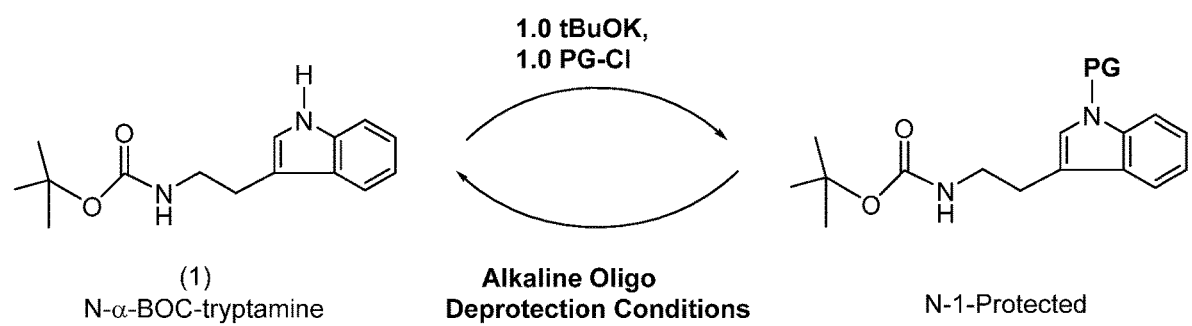
FIG. 2. Synthesis scheme for N-1-protected tryptamine compounds.
Figure 3:
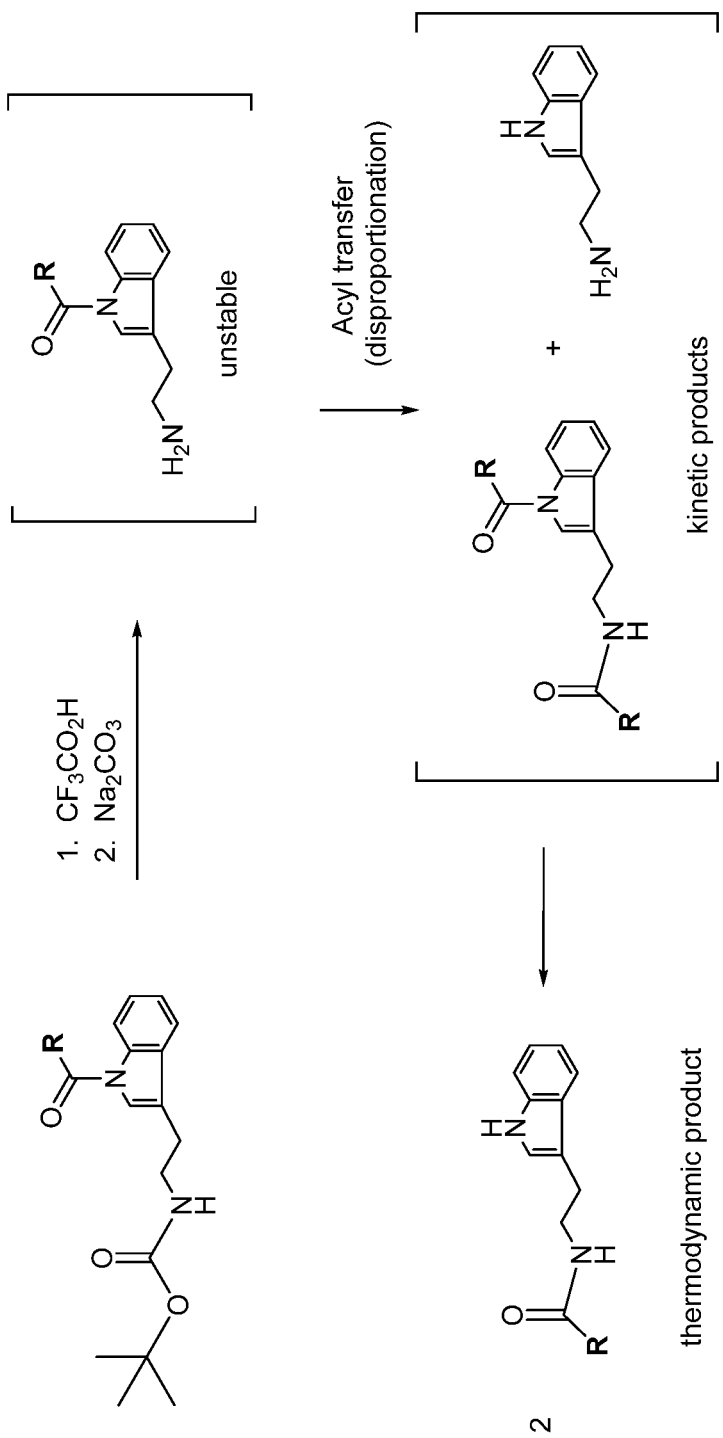
FIG. 3. Migration of acyl group in protected tryptamine following removal of BOC.

A model system was used to determine the reactivity of various sulfonyl- and acyl-protecting groups under standard oligonucleotide deprotection conditions. The compound, N-α-tert-butoxycarbonyltryptamine (FIG. 2, (1)), was used as a model for TrpdU. Various N-1 derivatives may be readily synthesized by treatment of (1) with potassium tert-butoxide (1.1 eq) in tetrahydrofuran (THF), followed by addition of the appropriate sulfonyl or acyl chloride or anhydride (1.0 eq) (FIG. 2). See Cole, D. C., et al, *J. Med. Chem.*, 50(23), 5535-5538, 2007. The resulting N-1 derivatives (Table 1) were purified by crystallization, chromatography, or used directly in deprotection tests.

TABLE 2

Model Conditions for Oligonucleotide Deprotection

| Condition | Standard deprotection reagent | Modified reagent (this study) |
|---|---|---|
| tBuNH$_2$ (tert-butylamine) | tBuNH$_2$:MeOH:H$_2$O (1:1:2) | tBuNH$_2$:MeOH:H$_2$O (1:2:1) |
| NH$_4$OH (ammonium hydroxide) | Conc NH$_4$OH (neat) | Conc. NH$_4$OH:MeOH (2:1) |

The target rate for alkaline cleavage of the protecting groups in the model system was defined by a mathematical model. It was assumed that the deprotection would follow pseudo-first order kinetics in the presence of excess base. The minimum acceptable rate was defined as 99.9% cleavage at 24 hours. The preferred reaction rate would give more margin for variability and was defined as 99.9% cleavage in 12 hours. Based on these criteria, the desired protecting group would be 25-44% cleaved at 1 hour and 68-90% cleaved at 4 hours and >/=99.9% cleaved at 24 hours.

TABLE 1

Reagents for Synthesis of N-1-Protected Analogs of a-BOC-Tryptamine.

| Acid chloride or anhydride | PG Name | Code | Source | Tryptamine N-1-analog | NB Reference |
|---|---|---|---|---|---|
| CH$_3$SO$_2$Cl | methanesulfonyl | Ms | Aldrich | resin | 2000-20-0 |
| 4-CH$_3$C$_6$H$_4$COCl | p-toluenesulfonyl | Ts | Aldrich | resin | 2000-21-0 |
| (CF$_3$SO$_2$)$_2$O | Trifluoromethanesulfonyl | Tf | Aldrich | crystalline | 2000-31-1 |
| (CH$_3$CO)$_2$O | acetyl | Ac | Aldrich | crystalline | 2000-26-1 |
| (CF$_3$CO)$_2$O | trifluoroacetyl | TFA | Aldrich | crystalline | 2000-24-1 |
| (C$_6$H$_5$CO)$_2$O | benzoyl | Bz | Aldrich | crystalline | 2000-30-1 |
| (CH$_3$)$_3$CCOCl | trimethylacetyl (pivaloyl) | Piv | Aldrich | crystalline | 2000-35-1 |
| 2,4,6-(CH$_3$)$_3$—C$_6$H$_2$COCl | trimethylbenzoyl (mesitoyl) | Ms | Alfa Aesar | crystalline | 2000-38-1 |
| 2,4,6-Cl$_3$—PhCOCl | trichlorobenzoyl | Tcb | Acros | crystalline | 2000-43-1 |
| 2-CH$_3$—C$_6$H$_4$COCl | o-toluoyl | Tol | Aldrich | resin | 2000-52-1 |
| Cl$_3$CCOCl | trichloroacetyl | Tc | Aldrich | Synthesis failed | 2000-25-1 |
| Cl$_3$CCH$_2$OCOCl | 2,2,2-trichloroethyl carbonate | TROC | Aldrich | wax | 2000-27-1 |
| (CH$_3$CH$_2$)$_3$CCOCl | 2,2-diethylbutyroyl [triethylacetyl] | Deb | Ethyl ester: Alfa Aesar 2000-39-1 | resin | 2000-41-1 |
| (CH$_3$CH$_2$)$_2$(CH$_3$)CCOCl | 2-ethyl-2methyl-butyroyl | Emb | 3 steps* 2000-50 | resin | 2000-49-1 |
| (CH$_3$CH$_2$)(CH$_3$)$_2$CCOCl | 2,2-dimethylbutyroyl | Dmb | Alfa Aesar | oil | 2000-42-1 |
| (CH$_3$CH$_2$CH$_2$)(CH$_3$)$_2$CCOCl | 2,2,-dimethylvaleroyl | Dmv | Acid: TCI America 2000-57 | resin | 2000-58-1 |
| ((CH$_3$)$_2$CH)(CH$_3$)$_2$CCOCl | 2,2,3-trimethylbutyroyl | Tmb | 2 steps** 2000-54-1 | resin | 2000-59-1 |
| 1-CH$_3$—(cC$_5$H$_{10}$)COCl | 1-methylcyclopentane carbonyl | Mcp | Acid: Aldrich 2000-66-1 | resin | 2000-66-1 |
| 1-CH$_3$—(cC$_6$H$_{12}$)COCl | 1-methylcyclohexane carbonyl | Mcb | Aldrich | resin | 2000-67-1 |
| (CH$_3$CH$_2$CH$_2$)$_2$CHCOCl | 2-n-propyl-butyroyl | Dpa | Alfa Aesar | oil | 2000-61-1 |

*Chuit, C., et al, *Tetrahedron*, 36(16), 2305-10, 1980; Kudo, Noriaki, K., et al, *Chem & Pharm Bull*. 44(4), 699-702, 1996; Hoffamn, W. F., et al, *J. Med. Chem.*, 29(5), 842-52, 1986.
**Takahashi, Y., et al, *Synthetic Communications*, 19(11-12), 1945-54, 1989; Fathi, B., et al, *Helvetica Chimica Acta*, 85(7), 2083-2088, 2002.

Deprotection test conditions were based on two protocols: tert-butylamine and ammonium hydroxide at 37° C. In order to dissolve the hydrophobic model compounds, methanol was added to the deprotection reagents (Table 2). Samples of each deprotection reaction at 37° C. were analyzed at 1, 4, and 24 hours. In some cases, the substrates were also subjected to a "Stress" deprotection condition of 70° C. for 24 hours.

The deprotection reactions were monitored by classical thin layer chromatography (TLC) on silica gel plates, eluting with 25% ethyl acetate/75% hexane. The most accurate TLC visualization technique was found to be alkaline permanganate stain. Iodine staining may result in over-representation of the unprotected indole, while UV light visualization may result in over-representation of the protected N-1 acyl derivatives.

Sulfonyl protecting groups were studied first. Three derivatives were synthesized to represent a range of structures and reactivities: trifluromethanesulfonyl (triflyl); methanesulfonyl (mesyl); and benzenesulfonyl (besyl) (Table 1). All three sulfonyl derivatives were found to be completely stable (0% cleaved) under the model oligo deprotection conditions (Table 3). It was concluded that the harsh alkaline conditions (NaOH+heat) described in the literature to cleave N-1-indole sulfonyl protecting groups are necessary and even the highly reactive trifluromethanesulfonyl (Tf) group is stable to milder oligo deprotection conditions.

A set of 16 acyl analogues (4 aryl and 12 alkyl) were synthesized from BOC-tryptamine and the appropriate acid chloride reagent. The 16 acid chlorides were obtained commercially, or synthesized from the commercially-available carboxylic acid by reaction with thionyl chloride, or synthesized de novo in 2-3 steps (Table 1).

The acyl protecting groups showed a range of reactivity to alkaline deprotection conditions. The four aryl acyl derivatives showed a spectrum of reactivity (Table 4). The unsubstituted benzoyl group was too reactive and completely cleaved in under 1 hour, whereas the 2,4,6-trisubsituted analogs, Mes and Tcb, were too stable and showed no detectable cleavage under standard conditions. Between those extremes was the moderately-hindered 2-methylbenzoyl (Tol) analog, which fit within the desired target cleavage rates. The Tol group was chosen for further evaluation.

None of the 12 alkyl acyl protecting groups met the desired target rate. The analogs were found to be either too reactive (Table 5) or too stable (Table 6). Small structural changes were found to dramatically change the alkaline cleavage rate. For example, dimethylethylacetyl (Dmb) is too fast whereas the diethylmethylacetyl (Meb) is too slow.

None of the too-stable analogs (Table 5) were considered for further development because incomplete deprotection is generally not acceptable in oligonucleotide synthesis.

There were five analogs in the too-fast group (Table 5) with roughly equivalent reactivity: Piv, Mcp, Mch, Dmv, and Dmb. All showed ~90% cleavage at 1 hour and 100% cleavage at 4 hours, which was faster than the desired target rates. Nonetheless, Piv and Dmb were selected for further evaluation.

In summary, the initial N-α-BOC-tryptamine model system allowed identification of three leads as possible N-1 protecting group: Tol, Dmb, and Piv. The three leads displayed a range of reactivity towards alkaline SOS deprotection conditions: Piv>Dmb>Tol.

TABLE 3

Percent Deprotection for Sulfonyl Groups ("Too Slow").

| Reagent | Condition | Target | Tf | Ms | Bs |
|---|---|---|---|---|---|
| tBuNH$_2$ | 37° C., 1 h | 25-44% | 0% | 0% | 0% |
| | 37° C., 4 h | 68-90% | 0% | 0% | 0% |
| | 37° C., 24 h | 100% | 0% | 0% | 0% |
| | 70° C., 24 h | 100% | 0% | 0% | 0% |
| NH$_4$OH | 37° C., 1 h | 25-44% | 0% | 0% | 0% |
| | 37° C., 4 h | 68-90% | 0% | 0% | 0% |
| | 37° C., 24 h | 100% | 0% | 0% | 0% |
| | 70° C., 24 h | 100% | 0% | 0% | 0% |

TABLE 4

Percent Deprotection for Aryl Acyl Groups ("Just Right" = Tol).

| Reagent | Condition | Target | Bz | Tol | Tcb | Mes |
|---|---|---|---|---|---|---|
| tBuNH$_2$ | 37° C., 1 h | 25-58% | 100% | 60% | 0% | 0% |
| | 37° C., 4 h | 68-99.9% | — | 95% | 0% | 0% |
| | 37° C., 24 h | 100% | — | 100% | 5% | 0% |
| | 70° C., 24 h | 100% | — | — | 50% | 0% |
| NH$_4$OH | 37° C., 1 h | 25-58% | 100% | 60% | 0% | 0% |
| | 37° C., 4 h | 68-99.9% | — | 95% | 0% | 0% |
| | 37° C., 24 h | 100% | — | 100% | 5% | 0% |
| | 70° C., 24 h | 100% | — | — | 50% | 0% |

TABLE 5

Percent Deprotection for Alkyl Acyl Groups ("Too Fast")

| Reagent | Condition | Target | TFA | Ac | Piv | Mcp | Mch | Dmv | Dmb |
|---|---|---|---|---|---|---|---|---|---|
| tBuNH$_2$ | 37° C., 1 h | 25-58% | 100% | 100% | 95% | 90% | 90% | 90% | 80% |
| | 37° C., 4 h | 68-99.9% | — | — | 100% | 100% | 100% | 100% | 100% |
| | 37° C., 24 h | 100% | — | — | — | — | — | — | — |
| | 70° C., 24 h | 100% | — | — | — | — | — | — | — |
| NH$_4$OH | 37° C., 1 h | 25-58% | 100% | >50% | 90% | 90% | 90% | 90% | 80% |
| | 37° C., 4 h | 68-99.9% | — | 100% | 100% | 100% | 100% | 100% | 100% |
| | 37° C., 24 h | 100% | — | — | — | — | — | — | — |
| | 70° C., 24 h | 100% | — | — | — | — | — | — | — |

TABLE 6

Percent Deprotection for Alkyl Acyl Groups ("Too Slow")

| Reagent | Condition | Target | Dpa | Tmb | Emb | Deb |
|---|---|---|---|---|---|---|
| tBuNH$_2$ | 37° C., 1 h | 25-58% | 20% | 20% | 20% | 0% |
| | 37° C., 4 h | 68-99.9% | 70% | 60% | 60% | 0% |
| | 37° C., 24 h | 100% | 98% | 95% | 90% | 0% |
| | 70° C., 24 h | 100% | — | 100% | 100% | 10% |
| NH$_4$OH | 37° C., 1 h | 25-58% | 20% | 10% | 20% | 0% |
| | 37° C., 4 h | 68-99.9% | 70% | 50% | 60% | 0% |
| | 37° C., 24 h | 100% | 95% | 95% | 90% | 0% |
| | 70° C., 24 h | 100% | — | 100% | 100% | 10% |

Example 2

Use of Selected Protecting Groups in TrpU

Figure 4:
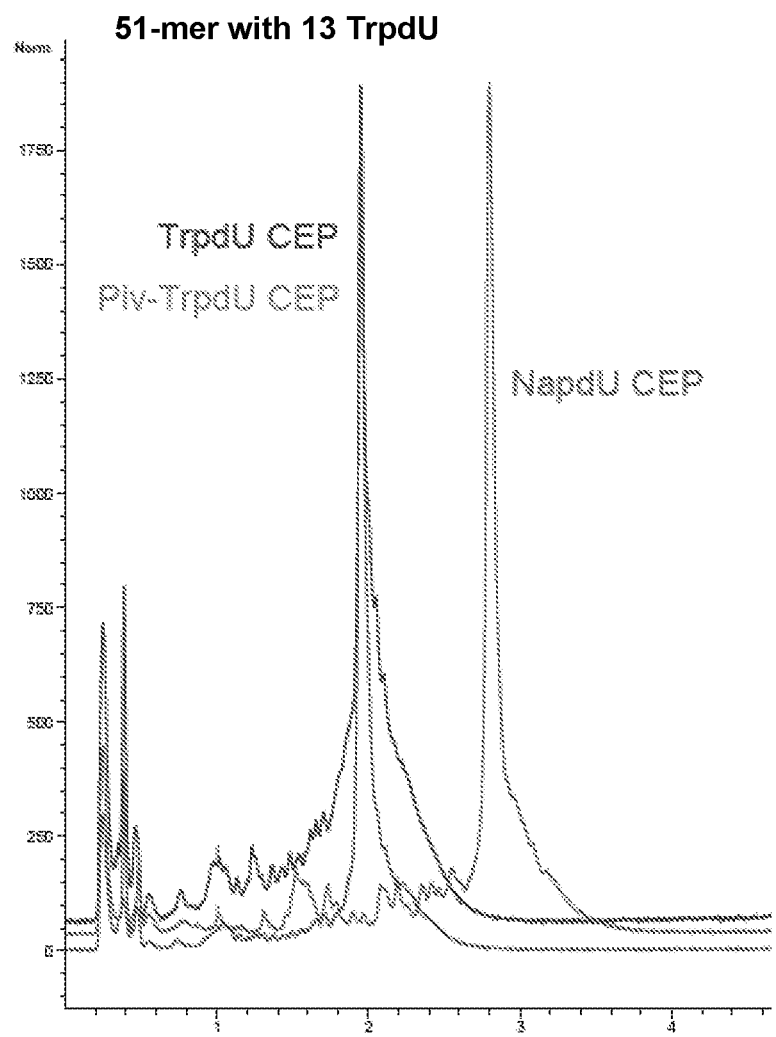
FIG. 4. HPLC profiles of aptamers synthesized using piv-TrpdU cyanoethyl-N,N-diisopropyl phosphoramidite (CEP), unprotected TrpdU CEP, and NapdU CEP.

The differing reactivities of the three N-1 protecting groups (Piv>Dmb>Tol) were observed after removal of the N-α-BOC group and conversion into free base form. The N-1 protected free base is unstable because the N-1 acyl group (aromatic amine) migrates to the N—α (primary alkyl amine), which forms a stronger amide bond (FIG. 4). This auto-degradative rearrangement is analogous to standard alkaline deprotection.

The three analogs, Piv>Dmb>Tol, were treated with trifluoracetic acid in dichloromethane to cleave the N-α-BOC protecting group. The reactions were quenched with 5% sodium carbonate and the N-1-protected tryptamine free bases were extracted with isopropyl acetate. A stability test was performed by heating the free base extracts (~100 mM) at 70° C. overnight. It was found that the Piv compound was completely decomposed, the Dmb compound was ~50% decomposed, and the Tol compound was <5% decomposed. A similar degree of degradation was observed when the extracts were concentrated on the rotovap and the pure amines were held overnight at room temperature. The extracts were found to be stable if stored in the freezer.

The three leads (Tol, Dmb, Piv) were next converted into the corresponding 5'-DMT-2'-deoxyuridine-5-carboxamides by removing the BOC group and condensing the N-1 protected tryptamines with 5'-O-DMT-5-(2,2,2-trifluoroethyoxy-carbonyl)-2'-deoxyuridine (TFEdU) to afford the N-1 protected TrpdU nucleosides: Tol-TrpdU, Dmb-TrpdU and Piv-TrpdU. In order to minimize autodegradation of the amines, the TFEdU was added directly to the dried extracts from the de-BOC reaction before concentration on the rotovap. It was found that by using this method, the desired reaction pathway predominates, yielding the pure 5'DMT-2'-deoxyuridine-5-carboxamides, which were purified by silica gel chromatography.

These nucleosides were then evaluated in the model alkaline deprotection tests (Table 7). It was found that cleavage of the acyl protecting groups, Tol and Dmb, was slower in the TrpdU nucleoside compounds than in the in initial BOC-tryptamine model (Table 6).

TABLE 7

Percent Deprotection for N-1-Protected TrpdU Nucleosides.

| Reagent | Condition | Target | Tol | Dmb | Piv |
|---------|-----------|--------|-----|-----|-----|
| tBuNH$_2$ | 37° C., 1 h | 25-44% | 10% | 70% | 95% |
|         | 37° C., 4 h | 68-90% | 50% | 100% | 100% |
|         | 37° C., 24 h | 100% | 90% | — | — |
|         | 70° C., 24 h | 100% | 100% | — | — |
| NH$_4$OH | 37° C., 1 h | 25-44% | 10% | 30% | 95% |
|         | 37° C., 4 h | 68-90% | 50% | 70% | 100% |
|         | 37° C., 24 h | 100% | 95% | 100% | — |
|         | 70° C., 24 h | 100% | 100% | — | — |

Example 3

Synthesis of Piv-TrpdU CEP

Figure 5:
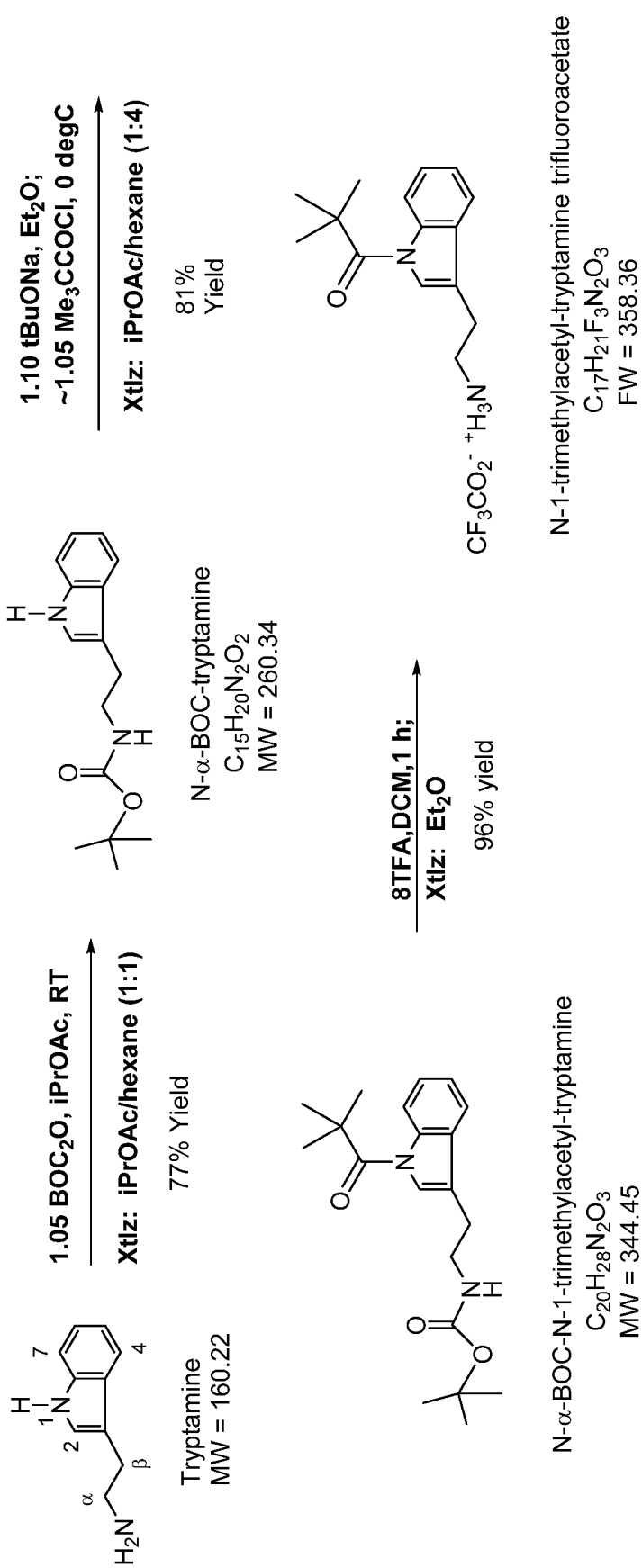
FIG. 5. Synthesis scheme for N-1-piv-tryptamine trifluoroacetate.
Figure 6:
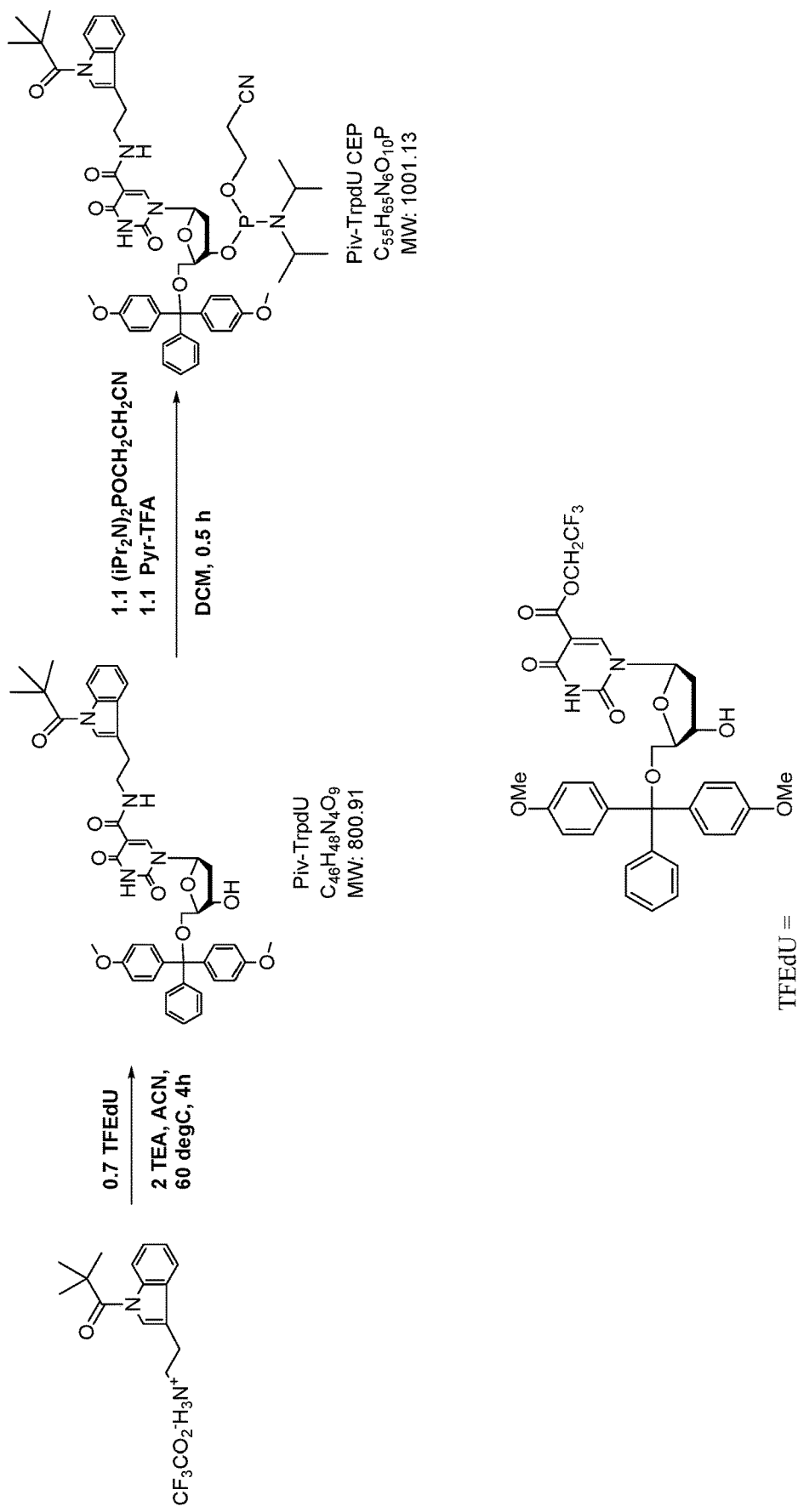
FIG. 6. Synthesis scheme for Piv-TrpdU cyanoethyl-N, N-diisopropyl phosphoramidite (CEP).

An efficient 3-step process to prepare the N-1-Piv-tryptamine side chain (as the stable trifluoroacetate [TFA] salt) was developed, which involves three crystalline intermediates and requires no chromatography. The TFA salt is then coupled with TFEdU. The complete process is shown in FIGS. 5 and 6.

N-α-BOC-tryptamine. A method of making N-α-BOC-tryptamine that avoids silica gel chromatography was developed. The use of isopropyl acetate as solvent allows the product to crystallize directly from the reaction mixture. See FIG. 5.

The starting material, tryptamine, is a granular crystalline solid, pale orange or light tan in color, such as is currently commercially-available from Alfa Aesar (product A11116). Brown, fecal-smelling tryptamine should be recrystallized before use. BOC anhydride (di-tent-butyl dicarbonate; product 205249), and all other solvents and reagents were purchased from Sigma-Aldrich and used as received.

A mechanically-stirred 1 round bottom flask was charged with tryptamine (49.32 g, 308 mmol), and isopropyl acetate (200 mL). The mixture was rapidly stirred under an argon bubbler and a solution of di-tent-butyl dicarbonate (70.53 g, 323 mmol) in isopropyl acetate (100 mL) was added dropwise over 30 minutes. Gas began to evolve steadily after ~40 mL had been added and all the solids dissolved near the end of the addition, affording a yellow solution. Stirring was continued for another 30 minutes and TLC check confirmed consumption of the starting tryptamine (SG60, 10% MeOH/90% dichloromethane, Rf(SM)=0.1, Rf(product)=0.8).

The solution was filtered to remove some sand and dust. The filtrate (~395 g) was concentrated on the rotovap to ~250 g and the warm (40° C.) solution was slowly diluted with hexanes (~220 mL), until the onset of cloudiness. The solution was seeded with 10 mg authentic product and immediately crystallized. The slurry was aged by stirring 1 hour at room temperature and 1 hour on ice, then filtered and rinsed forward with 25% iPrOAc/75% hexanes (75 mL). The filter cake was washed with hexanes (100 mL) and dried in vacuo to afford the N-α-BOC-tryptamine as a white crystalline solid (mp 86-88° C.), 61.75 g, 77% yield.

N-α-BOC-N-1-trimethylacetyl-tryptamine. Based on the work of Cole, D. C., et al, *J. Med. Chem.*, 50(23), 5535-5538, 2007, potassium tert-butoxide in THF was initially used as the base and solvent for the reaction, but ~5% of a polar dimer byproduct (exact structure not determined) was produced, which was difficult to remove by crystallization. Several solvent and base combinations were tried, which revealed that the dimer byproduct could be suppressed by using sodium tert-butoxide in diethyl ether. The trimethylacetyl chloride was added in small portions at the end to titrate the N-1 anion, without generating over-acylated byproducts. See FIG. 5.

A dry, argon-filled 1 round bottom flask with a large (1.5") magnetic stir bar was charged with N-α-BOC-tryptamine (28.63 g, 110 mmol) and sodium tert-butoxide powder (11.63 g, 121 mmol, caution: irritant dust). Diethyl ether (anhydrous, 400 mL) was added by cannulla under argon and stirring for 10 min afforded a smooth, chalky slurry. A calibrated addition funnel was placed, charged with a solution of trimethylacetyl chloride (14.6 g, 121 mmol, 110% theory) in diethyl ether (~50 mL), for a total volume of 60 mL. The slurry was cooled in ice and rapidly stirred as most of the acid chloride solution (54.5 mL, 110 mmol, 100% theory) was added dropwise over ~40 min. The solution was stirred for another 20 min and sampled for TLC [0.2 mL aliquot in 1 mL dichloromethane] (SG60, 25% ethylacetate/75% hexanes; Rf(SM)=0.2, Rf(product)=0.4). If starting material is detectable (>1%), then a corresponding additional charge of acid chloride solution is added (1-10% theory, as indicated by TLC analysis) and stirring continued for 1 hour.

The reaction was quenched with 5% sodium bicarbonate (200 mL) and isopropyl acetate (100 mL). The organic layer was washed with NaCl brine (50 mL), dried with MgSO$_4$, filtered, and evaporated to dryness in vacuo to afford a tan solid (~37 g). This crude product was recrystallized from a hot solution of isopropyl acetate (74 mL) and hexanes (296 mL). Upon cooling to ~35° C., the stirred solution was seeded with authentic product (50 mg) and immediately crystallized. The slurry was rapidly stirred 1 hour at room temperature and 1 hour on ice. The slurry was filtered, rinsed forward with a portion of filtrate (30 mL), and then the cake was washed with hexanes (60 mL) and dried in vacuo.

N-α-BOC-N-1-trimethylacetyl-tryptamine was obtained as a white to off-white crystalline solid (mp 95-97° C.), 30.7 g, 81% yield.

If desired, the product may be reprocessed by additional recrystallizations from isopropyl acetate (2 mL/g) and hexanes (8 mL/g).

N-1-trimethylacetyl-tryptamine trifluoroacetate. This salt is a white crystalline solid that filters and washes easily and is stable and non-hygroscopic. The salt crystallizes directly from the reaction mixture. See FIG. 5.

A 500 mL round bottom flask was fitted with a Claisen adapter and oil bubbler configured to slowly sweep the headspace with argon. This facilitates removal of isobutylene gas from the reaction mixture and reduces side products.

A 500 mL round bottom flask (configured as above), with a large magnetic stir bar, was charged with N-α-BOC-N-1-trimethylacetyl-tryptamine (30.0 g, 87.1 mmol) dissolved in anhydrous dichloromethane (90 mL), and trifluoroacetic acid (53 mL, 693 mmol, 8 equiv.) was added. The solution was rapidly stirred as isobutylene gas evolved and was swept out through the oil bubbler. After 1 hour, crystals began to form in the mixture and TLC analysis showed the starting material was completely consumed (SG60, 25% ethyl acetate/75% hexanes; Rf(SM)=0.4; RF(product)=O). Diethyl ether (~275 mL) was added dropwise to the well-stirred mixture, causing it to thicken, and the resulting slurry was rapidly stirred for 1 hour at room temperature. Some soft wall cake was knocked down with the stir bar and the slurry was filtered and rinsed forward with diethyl ether (100 mL). The cake was carefully washed with diethyl ether (100 mL) and dried in vacuo to afford N-1-trimethylacetyl-tryptamine trifluoroacetate salt as a white, crystalline powder (mp 150-152° C.), 30.0 g, 96% yield.

N-1-trimethylacetyl-tryptamine trifluoroacetate salt is not significantly hygroscopic and can be shipped at ambient temperature, with protection from light in a tightly-sealed container. Informal stability tests showed that the salt was stable at 70° C. for ten days in a sealed vial. For long-term storage (>1 month), refrigerated or frozen storage conditions may be used as a precaution.

A summary of $^1$H-NMR characteristics of certain tryptamine compounds is shown in Table 8.

TABLE 8

$^1$H-NMR Summary for Tryptamine Compounds (ppm vs TMS).

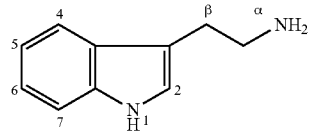 [SMILES: NCCc1c[nH]c2ccccc12]

| | Starting Material | Intermediate | Intermediate | Intermediate | Byproduct | Byproduct |
|---|---|---|---|---|---|---|
| 300 MHz | tryptamine | N-α-BOC-Trp | N-α-BOC-N-1-Piv-Trp | N-1-Piv-Trp•TFA | N-α-N-1-di-Piv-Trp | N-α-Piv-Trp |
| Solvent | DMSO-d6 | CDCl3 | CDCl3 | DMSO-d6 | CDCl3 | CDCl3 |
| α-CH2 | 2.73-2.83 m | 3.50, m | 3.49, m | 3.17, t, J = 7 Hz | 3.61, q, J = 7 Hz | 3.61, q, J = 7 Hz |
| β-CH2 | 2.73-2.83 m | 2.99, bt, J = 6.8 Hz | 2.94, bt, J = 6.8 Hz | 3.05, t, J = 7 Hz | 2.94, dt, J = 1.7 Hz | 3.00, q, J = 7 Hz |
| N-1-H | 10.79 bs | 8.33 bs | none | none | none | 8.76 bs |
| N-α-H | 1.31, 2H, bs, | 4.70 bs | 4.73 bs | 8.14, 3H, vbs (NH$_3^+$) | 5.89, bt, J = 7 Hz | 5.85 bs |
| 2-H | 7.12 bd, J = 2 Hz | 7.02, sbs | 7.58, bs | 8.00, sbs | 7.57, bs | 7.01, d, J = 2 Hz |
| 4-H | 7.51, bd, J = 8 Hz | 7.64, bd, J = 8 Hz | 7.54, bd, J = 7 Hz | 7.65, dd, J = 1.8 Hz | 7.55, bd, J = 8 Hz | 7.64 d J = 8 Hz |
| 5-H | 6.96, dt, J = 1.8 Hz | 7.16, dt, J = 1.8 Hz | 7.29, dt, J = 1.7 Hz | 7.29, dt, J = 1.8 Hz | 7.27, dt, J = 1.8 Hz | 7.14 dt J = 1.8 Hz |
| 6-H | 7.05, dt, J = 1.8 Hz | 7.24, dt, J = 1.8 Hz | 7.36, dt, J = 1.7 Hz | 7.34, dt, J = 1.8 Hz | 7.35, dt J = 1.8 Hz | 7.22 dt J = 1.8 Hz |
| 7-H | 7.33, dt, J = 8.1 Hz | 7.39, dd, J = 1.8 Hz | 8.52, dd, J = 1.8 Hz | 8.40, bd, J = 8 Hz | 8.51, dt, J = 8.1 Hz | 7.39, dt, J = 8.1 Hz |
| BOC | none | 1.49, s, 9H | 1.52, s, 9H | none | none | none |
| Piv | none | none | 1.45, bs, 9H | 1.45, s, 9H | 1.49, N-1, s, 9H 1.15, N-α, s, 9H | 1.16, s, 9H |
| Ref | 2000-88-SM | 1488-133, 2000-88 | 2000-90 | 2000-113 | 2000-85-F5, 2000-121 | 2000-120-1 |
| MW | 160.22 | 260.34 | 344.45 | 358.36 | 328.46 | 244.34 |
| MS⁻ (found) | 144.1/161.1 (MS⁺) | 259.1 | 343.1 | no test | 327.2 | no test |
| 19FNMR | none | none | none | 73.64 s | none | none |

5'-O-(4,4'-Dimethoxytrityl)-5-[N-(((N-1-trimethyacetyl)-3-indole)-2-ethyl)carboxamide]-2'-deoxyuridine (Piv-TrpdU). A 200 mL round bottom flask was charged with 5'-O-DMT-5-(2,2,2-trifluoroethyoxy-carbonyl)-2'-deoxyuridine (TFEdU, technical grade ca. 90%, 13.1 g, 20 mmol uncorrected) and N-1-trimethylacetyl-trypatamine trifluoroacetate salt (9.23 g, 26 mmol, 1.3 eq). Anhydrous acetonitrile (104 mL) was added by syringe, followed by triethylamine (5.6 mL, 40 mmol, 2.0 eq). The resulting orange solution was heated under argon at 60° C. for 24 hours. A 0.1 mL aliquot was removed and diluted with dichlorormethane for TLC analysis (SG60, eluent: 1:1 acetone:hexane). See FIG. 6. If TFEdU starting material remains detectable (>1%), then a corresponding charge (1-5%) of additional N-1-trimethylacetyl-trypatamine trifluoroacetate is added and heating is continued. If TFEdU is consumed (<1%), then the reaction mixture is evaporated to a foam on the rotovap. Redissolve the foam (~33 g) in dichloromethane (30 mL) for chromatography.

A 4"D×6"H flash silica gel column was conditioned with 2/2/96 TEA/MeOH/DCM (4 L), then flushed with 2/98 MeOH/DCM (2 L). The crude product was applied and eluted with 1/99 MeOH/DCM (2 L), followed by 2/98 MeOH/DCM. Fractions (250 mL) were collected and pooling fractions 8-19 gave piv-TrpdU nucleoside as a pale yellow solid, 14.8 g (66% yield). Handle the wet solid under argon to minimize yellowing.

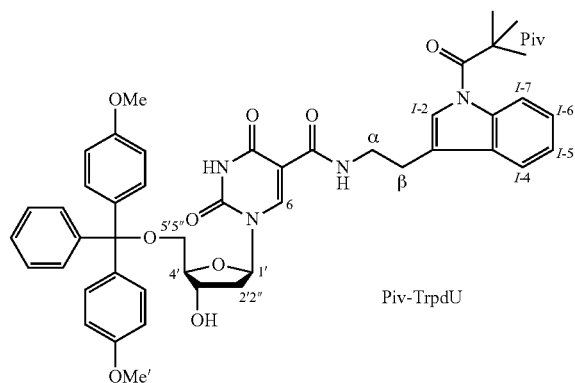

Piv-TrpdU

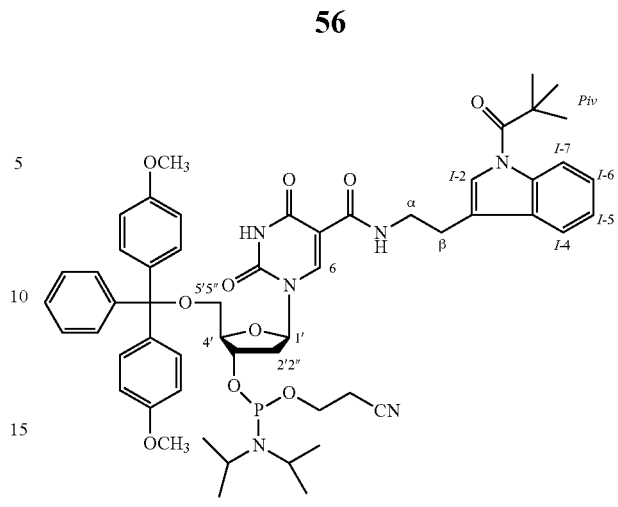

Piv-TrpdU CEP
Chemical Formula: $C_{55}H_{65}N_6O_{10}P$
Molecular Weight: 1001.13

$^1$H-NMR (CD$_3$CN, 300 MHz): δ 8.76 (1H, t, J=6 Hz, CONHCH$_2$), 8.54 (s, 1H, H-6), 8.41 (1H, bd, J=8 Hz, I-7), 7.73 (1H, bs, I-2), 7.60 (1H, dt, J=8,1 Hz, I-4), 6.81-7.43 (15H, m, trityl and I-5 and I-6, overlapping), 6.09 (1H, t, J=6.5 Hz, H-1'), 4.24-4.28 (1H, m, H-3'), 3.98 (1H, q, J=4 Hz, H-4'), 3.701 (3H, s, MeO), 3.700 (3H, s, MeO'), 3.62-3.69 (2H, m, CH$_2$-α), 3.25-3.27 (2H, m, H-5' and H-5"), 2.95 (2H, t, J =6.8 Hz, CH$_2$-β), 2.18-2.34 (2H, m, H-2' and H-2"), 1.41 (9H, s, Piv).

$^{13}$C-NMR (CD$_3$CN, 100 MHz, 33×C): δ 177.0, 163.0, 161.8, 158.6, 149.5, 145.6, 145.1, 137.1, 135.8, 130.1, 129.5, 128.0, 127.9, 126.8, 125.0, 123.8, 123.2, 118.7, 118.6, 117.0, 113.1, 105.7, 86.3, 86.2, 71.0, 63.6, 54.8, 40.9, 40.2, 38.3, 27.8, 24.8.

Mass Spec [M−H]$^−$: calculated for C$_{46}$H$_{48}$N$_4$O$_9$: 800.91; experimental: 799.3.

5'-O-(4,4'-Dimethoxytrityl)-5-[N-(((N-1-trimethyacetyl)-3-indole)-2-ethyl)carboxamide]-2'-deoxyuridine-3'-O—(N,N-diisopropyl-O-2-cyanoethylphosphoramidite (Piv-TrpdU CEP). All chromatography solvents were deoxygenated by sparging with argon using a fine gas dispersion tube. In preparation for the reaction, a 6"D×6"H flash silica gel column was conditioned with 2/30/68 Et$_3$N/hexanes/EtOAc (8 L) and then flushed with 30/70 hexanes/EtOAc (4 L). Additional 30/70 eluent (16 L) was prepared and degassed.

A dry round-bottom flask was charged under argon with Piv-TrpdU (41.3 g, 51.5 mmol), anhydrous dichloromethane (83 mL), 2-cyanoethyl-N,N,N',N'-tetraisopropylphosphoramidite (18.0 mL, 56.7 mmol, 1.1 eq), and finally, pyridine trifluoroacetate powder (10.95 g, 56.7 mmol, 1.1 eq). The mixture was rapidly stirred, affording a yellow solution, and after 30 minutes, an aliquot was withdrawn for TLC analysis (SG60, eluent: 1/1 EtOAc/hexane) which showed the starting material was consumed and two nonpolar products formed. See FIG. 6.

The entire reaction mixture was applied to the prepared flash column and eluted with 30/70 hexanes/EtOAc, collecting 10×0.5, then 10×1, fractions in argon-filled, capped serum bottles. The product (two diastereomers) was collected from pooled fractions 8-17, which were evaporated under argon, polish filtered, and chased with anhydrous ACN (2×500 mL). Drying at high vacuum afforded Piv-TrpdU CEP as an off-white foam (42.9 g, 83% yield).

$^1$H-NMR (CD$_3$CN, 300 MHz) δ 9.61 (1H, bs, NH-3), 8.73/8.72 (1H, 2bt, J=5.6/5.6 Hz, CONHCH$_2$), 8.58/8.56 (1H, 2s, H-6), 8.43/8.41 (1H, 2bd, J=8 Hz, Indole-7), 7.74 (1H, bs, Indole-2), 7.60 (1H, bd, J=8 Hz, Indole-4), 6.83-7.45 (15 H, m, 13×trityl and Indole-5 and Indole-6, overlapping), 6.11/6.09 (1H, 2t, J=6.6/6.6 Hz), 3.72 (3H, s, OMe), 4.38-4.47 (1H, m, H-3'), 4.12-4.15 (1H, m, H-4'), 3.71 (3H, s, OMe'), 3.51-3.76 (6H, m, CONHCH$_2$, 2×Me$_2$CH, CH$_2$CH$_2$CN, overlapping), 3.29-3.35 (2H, m, H-5' and H-5"), 2.50/2.61 (2H, 2t, J=6/6 Hz, CH$_2$CN), 2.27-2.54 (2H, m, H-2' and H-2"), 1.41 (9H, s, Piv), 1.01-1.16 (12H, m, 2×[CH$_3$]$_2$CH).

$^{31}$P-NMR (CD$_3$CN, 161 MHz) δ 148.12, 148.09.

Additional analytical data summary and a development batch history for the three N-1-protected-TrpdU CEP analogs is provided in Table 9.

TABLE 9

Development Batch History for N-1-Protected-TrpdU CEP Analogs

| CEP Lot | Analog | Nucleoside SM (lot) | CEP Yield And color | MW CEP | [M − H]$^−$ (found) | HPLC: (Σ 2 isomers) | $^1$H & $^{31}$P NMR |
|---|---|---|---|---|---|---|---|
| Lot 1 | Tol-TrpdU | 6.0 g (2000-62-1) | 6.0 g (80%) white | 1035.15 | 1033.3/ 1034.3 | 99.04% | pass |
| Lot 1 | Dmb-TrpdU | 5.9 g (2000-76-1) | 3.4 g (47%) white | 1015.16 | 1013.4/ 1014.4 | 99.39% | pass |
| Lot 1 | Piv-TrpdU | 10.8 g (2000-85-1) | 11.0 g (81%) white | 1001.1 | 999.3/ 1000.3 | 99.69% | pass |
| Lot 2 | Piv-TrpdU | 41.3 g (4 lots = <99.26%> HPLC) | 42.9 g (83%) white | 1001.1 | 999.4/ 1000.4 | 99.43% | pass |

Example 4

Use of Selected Protecting Groups in TrpdU Phosphoramidites

The three lead N-1 protected analogs, Tol-TrpdU, Dmb-TrpdU and Piv-TrpdU, were converted into cyanoethyl-N, N-diisopropyl phosphoramidites (CEPs), substantially as discussed above, and their use was evaluated in solid-phase oligonucleotide synthesis.

All three protected TrpdU CEP's worked well in solid-phase oligonucleotide synthesis, but Tol-TrpdU showed incomplete deprotection in some cases, consistent with the nucleoside model system (Table 7). Dmb-TrpdU and Piv-TrpdU were both completely deprotected under all standard conditions (tBuNH2/MeOH/$H_2O$; $MeNH_2$ (gas)).

Aptamers having the same nucleotide sequence were synthesized with either Piv-TrpdU CEP, the original unprotected TrpdU CEP or NapdU CEP (positive control; Table 10) with each modified dU occupying the U base position in the sequence. The aptamer is a 51-mer having 13 dU position residues.

TABLE 10

Aptamers synthesized using Piv-TrpdU, TrpdU, and NapdU

| CEP Reagent: | Aptamer | Length | # TrpdU | Area % FL |
|---|---|---|---|---|
| TrpdU | Aptamer 1 | 51 | 13 | 25.1 |
| Piv-TrpdU | Aptamer 2 | 51 | 13 | 44.1 |
| NapdU | Aptamer 3 | 51 | 0 | 45.6 |

FIG. 4 shows the results for the three aptamers having either the Piv-TrpdU, TrpdU, and NapdU incorporated. Unprotected TrpdU CEP gives a broad peak with many early and late-eluting byproducts. Piv-TrpdU CEP gives a notably cleaner profile with a narrow peak-width, comparable to control aptamer having the NapdU CEP.

The Piv-TrpdU CEP was used to synthesize six different aptamers to demonstrate the improvement in yield using the new phosphoramidite over the unprotected TrpdU. The first four aptamers in Table 11 (Aptamers 1 to 4) were synthesized on a MerMade synthesizer (AME Bioscience) at 1 µmol scale using standard conditions, and have previously resulted in low yields using unprotected TrpdU. The fifth aptamer in table 11 (Aptamer 5) was synthesized on an ABI synthesizer using standard workflow and deprotection conditions, and showed acceptable yields with unprotected TrpdU. The sixth aptamer (Aptamer 6) was synthesized on an ABI synthesizer using standard workflow and deprotection conditions, and previously resulted in low yields using unprotected TrpdU.

Table 11 shows the results of that experiment.

TABLE 11

Synthetic yields (% full length SOMAmer) using Piv-TrpdU versus TrpdU

| Aptamer | Length (nts.) | # dU Positions | TrpdU CEP % FL | Piv-TrpdU CEP % FL |
|---|---|---|---|---|
| Aptamer 1 | 74 | 12 | 17.5 | 37.1 |
| Aptamer 2 | 74 | 13 | 11.0 | 35.7 |
| Aptamer 3 | 74 | 13 | 13.0 | 43.5 |
| Aptamer 4 | 49 | 11 | 17.0 | 42.0 |
| Aptamer 5 | 50 | 13 | 57.0 | 72.0 |
| Aptamer 6 | 38 | 11 | 22 | 55.8 |
|  |  |  |  | 56.4 (2 runs) |

The use of the Piv-TrpdU CEP in oligonucleotide synthesis for aptamers 1-4 and 6 increased the synthetic yield of aptamers to about 250-300% of synthetic yields of aptamer with the unprotected TrpdU. The use of the Piv-TrpdU CEP in oligonucleotide synthesis for aptamer 5 increased the synthetic yield by about 25% over the synthetic yield of the aptamer with the unprotected with TrpdU. Thus, while different synthesizers may provide different yields, the general trend is that the use of the Piv-TrpdU CEP improves oligonucleotide synthesis yields compared to the use of the unprotected TrpdU.

I claim:

1. A compound having the structure:

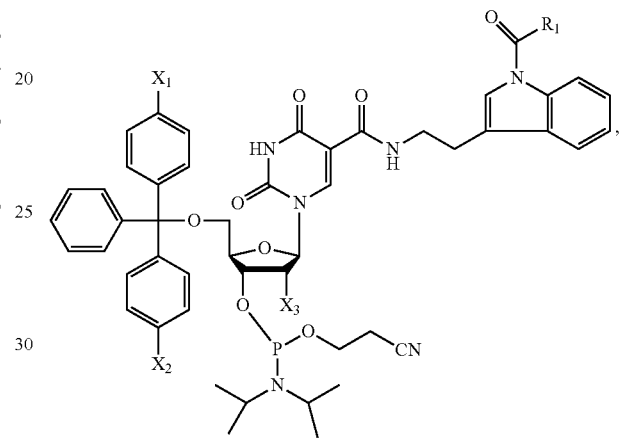

or a salt thereof;

wherein, $R_1$ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

$X_1$ and $X_2$ are each independently selected from methoxy and hydrogen; and $X_3$ is selected from methoxy, fluoro, hydrogen, and tert-butyldimethylsilyloxy.

2. The compound of claim 1, selected from:

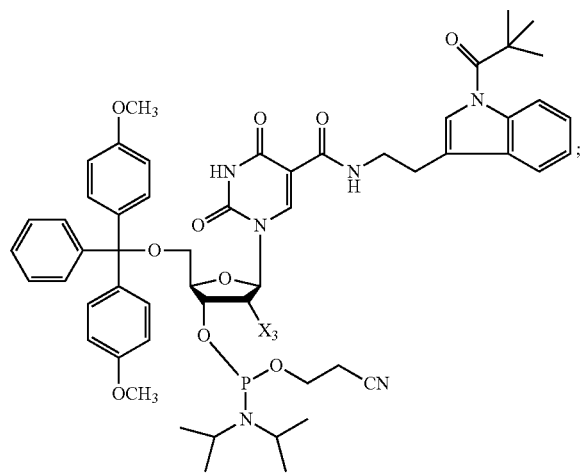

59
-continued
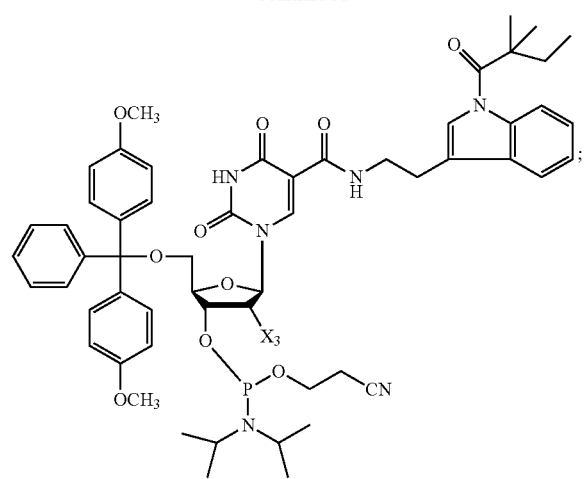
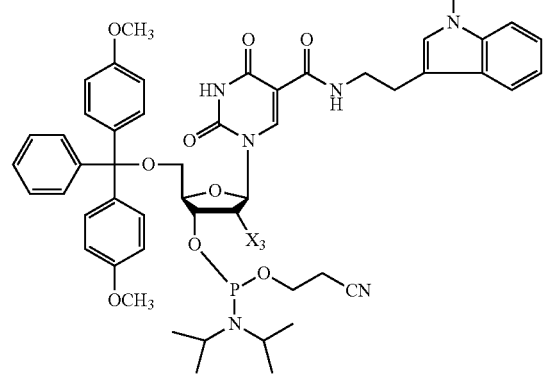
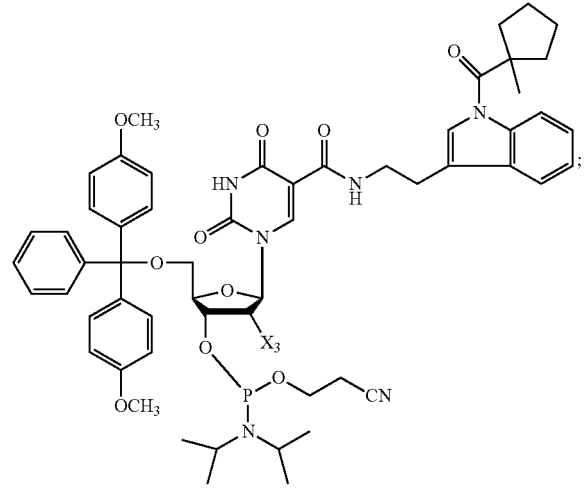
60
-continued
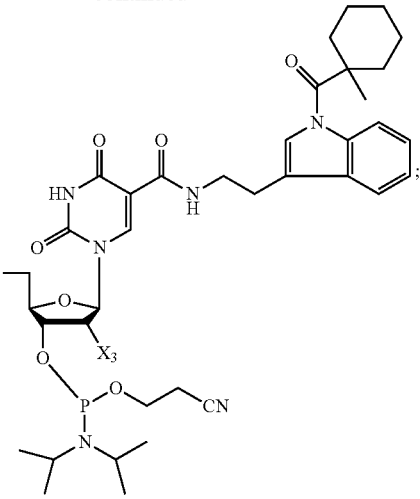
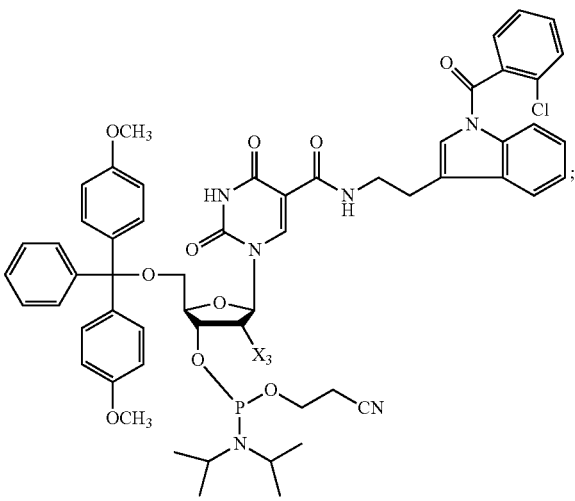
and salts thereof.

3. A compound having the structure:

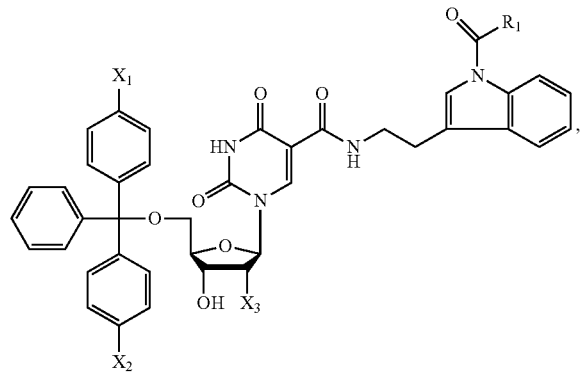

or a salt thereof;
wherein,
   $R_1$ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;
   $X_1$ and $X_2$ are each independently selected from methoxy and hydrogen; and
   $X_3$ is selected from a methoxy, fluoro, hydrogen, and tert-butyldimethylsilyloxy.

4. The compound of claim 3, selected from:

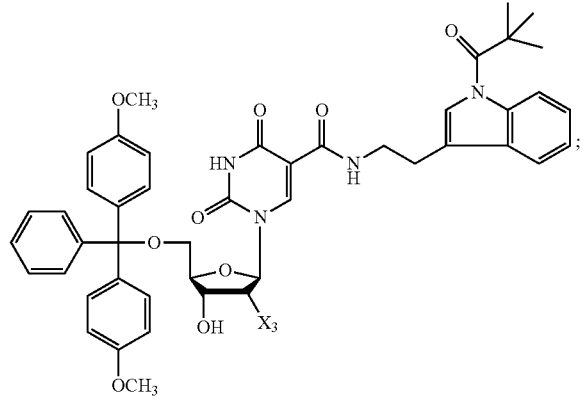

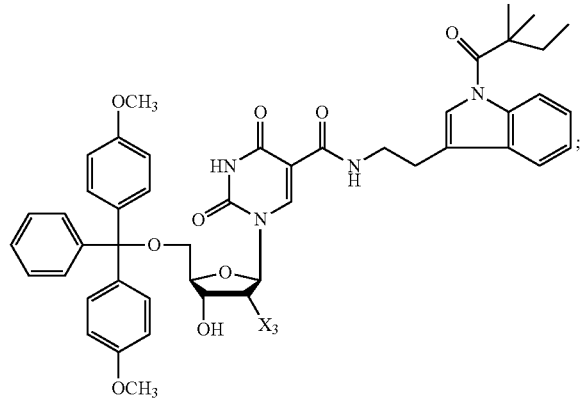

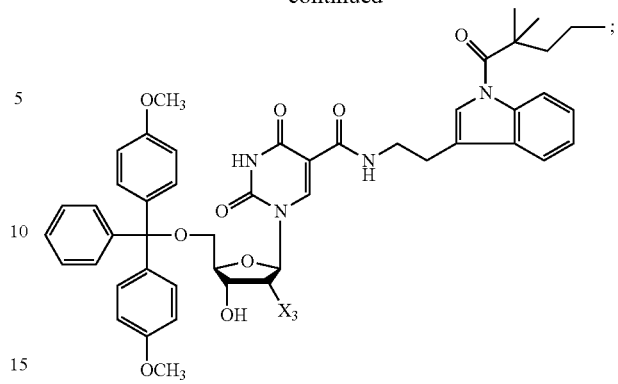

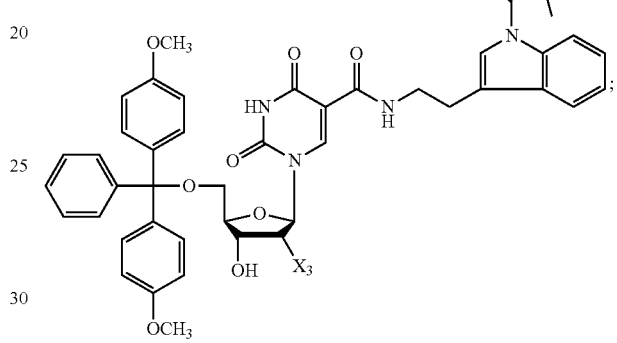

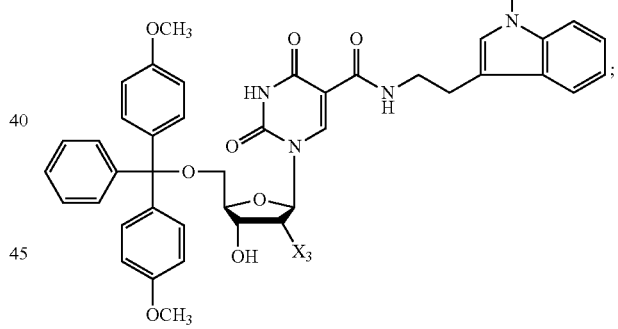

and salts thereof.

5. A compound having the structure:

or a salt thereof;
wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl.

6. The compound of claim 5, wherein the compound is:

or a salt thereof.

7. A compound having the structure:

wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl.

8. The compound of claim 7, wherein the compound is:

9. A method of producing a compound having the structure:

or a salt thereof;
wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;
the method comprising reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride.

10. The method of claim 9, wherein R₁ is tent-butyl, and wherein the acid chloride is pivaloyl chloride.

11. The method of claim 9, wherein the compound is:

12. A method of producing a compound having the structure:

wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

the method comprising reacting the compound

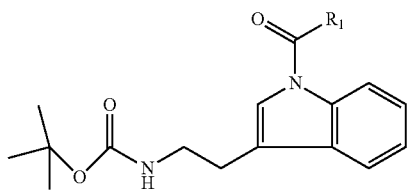

with trifluoroacetic acid.

13. The method of claim 12, wherein the method produces a compound of the structure:

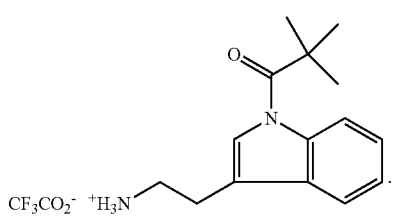 [SMILES: "CF3CO2-" ; CC(C)(C)C(=O)n1cc(CC[NH3+])c2ccccc21]

14. A method of producing a compound having the structure:

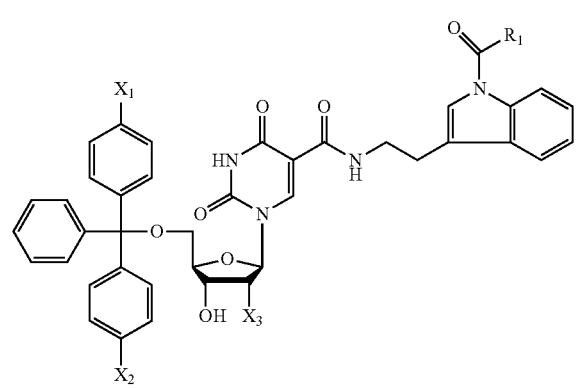

or a salt thereof;
wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;
X₁ and X₂ are each independently selected from methoxy and hydrogen;
X₃ is selected from a methoxy, fluoro, hydrogen, and tert-butyldimethylsilyloxy;
the method comprising reacting the compound

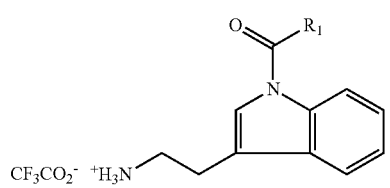

with 5'-O-DMT-5-(2,2,2-trifluoroethyoxy-carbonyl)-2'-deoxyuridine (TFEdU).

15. The method of claim 14, wherein the method produces a compound selected from:

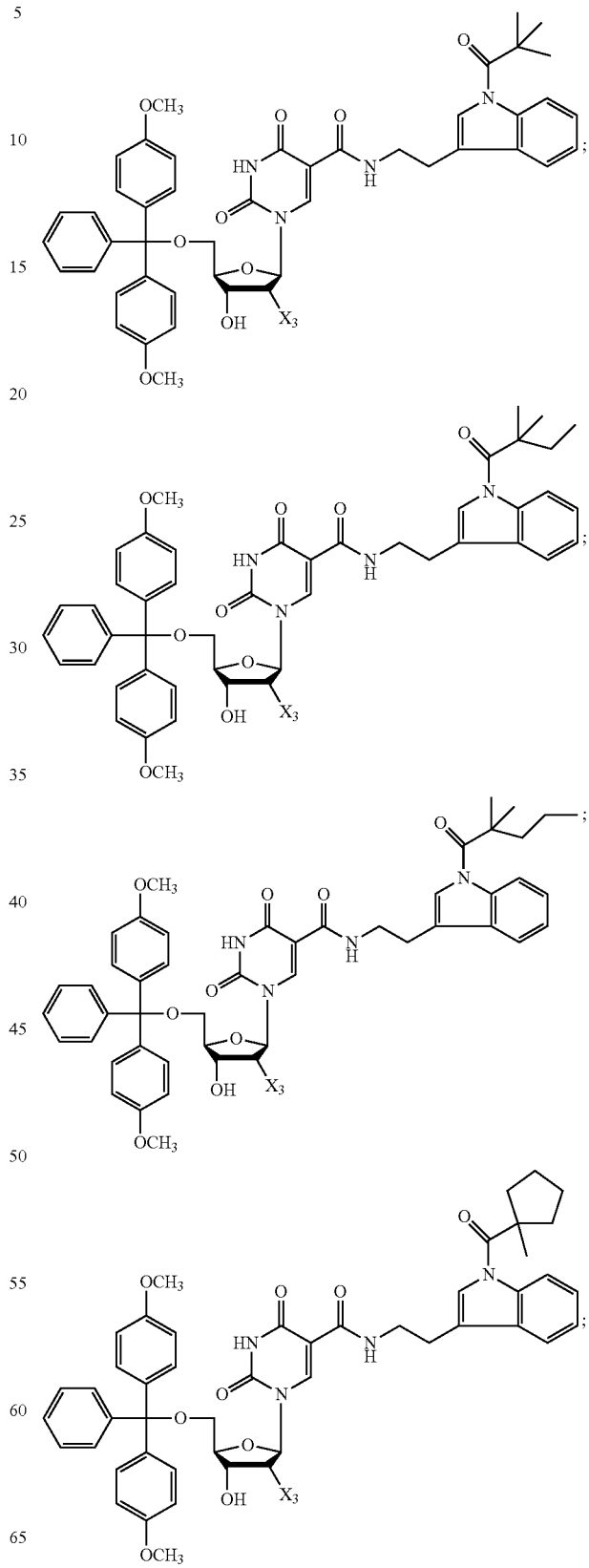

-continued

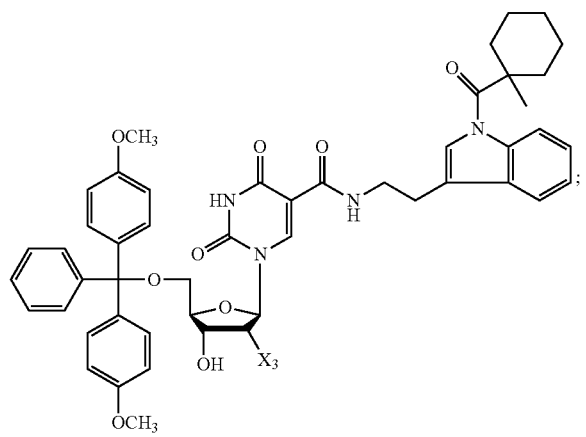

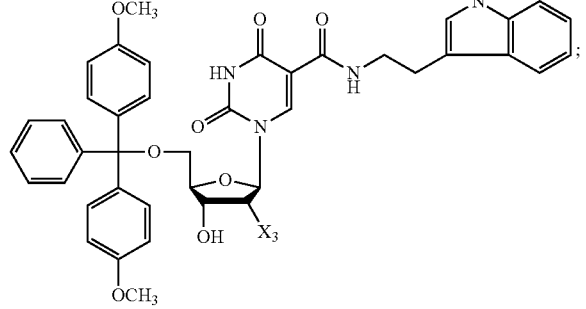

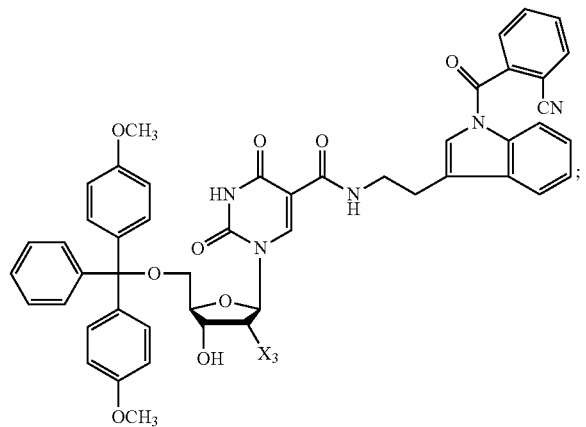

and salts thereof.

16. The method of claim 14, wherein the method further comprises reacting the compound

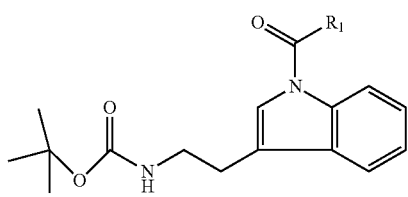

with trifluoroacetic acid to form the compound

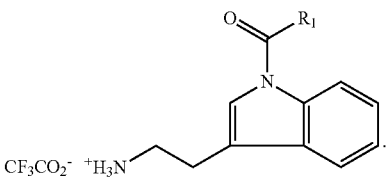

17. The method of claim 16, wherein the method further comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

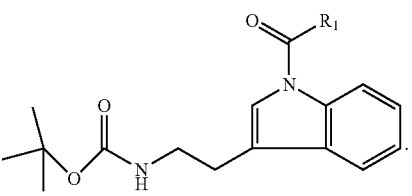

18. A method of producing a compound having the structure:

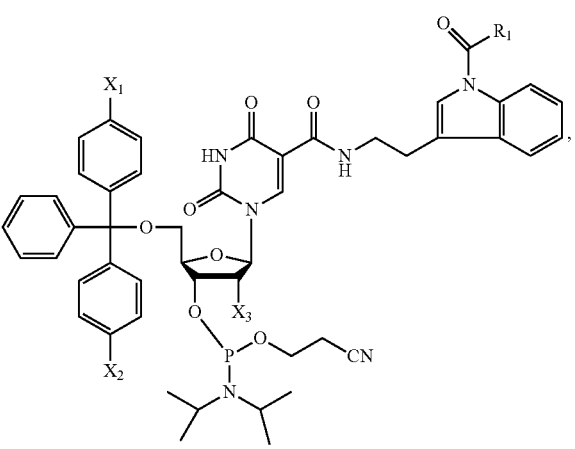

or a salt thereof;

wherein, $R_1$ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

$X_1$ and $X_2$ are each independently selected from methoxy and hydrogen;

$X_3$ is selected from a methoxy, fluoro, hydrogen, and tert-butyldimethylsilyloxy;

the method comprising reacting the compound

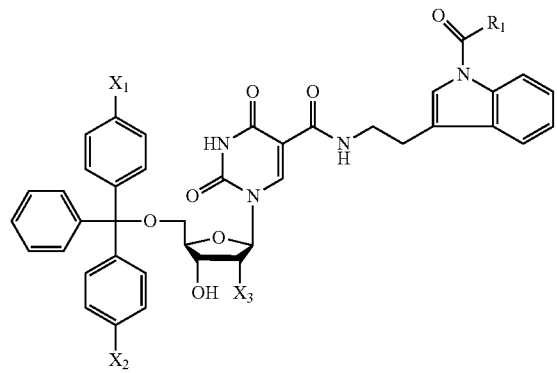

with 2-cyanoethyl-N,N,N',N'-tetraisopropylphosphoramidite.

19. The method of claim 18, wherein the method comprises reacting the compound

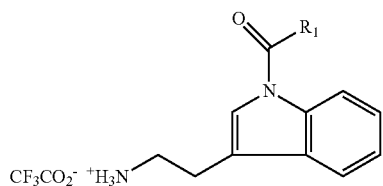

with 5'-O-DMT-5-(2,2,2-trifluoroethyoxy-carbonyl)- 2'-deoxyuridine (TFEdU) to form the compound

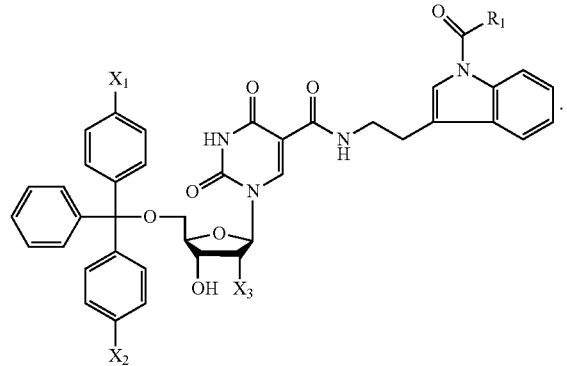

20. The method of claim 19, wherein the method comprises reacting the compound

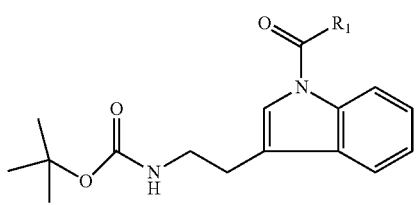

with trifluoroacetic acid to form the compound

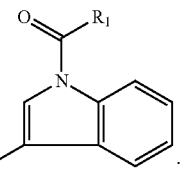

21. The method of claim 20, wherein the method comprises reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

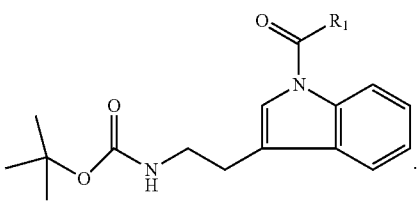

22. The method of claim 18, which produces a compound selected from:

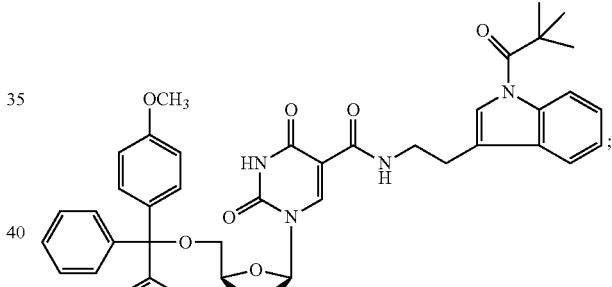

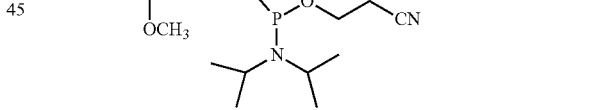

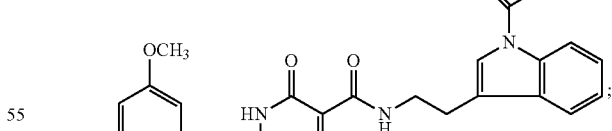

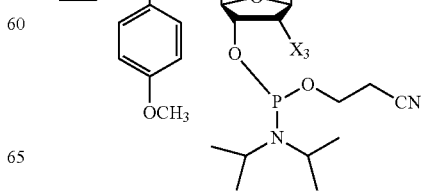

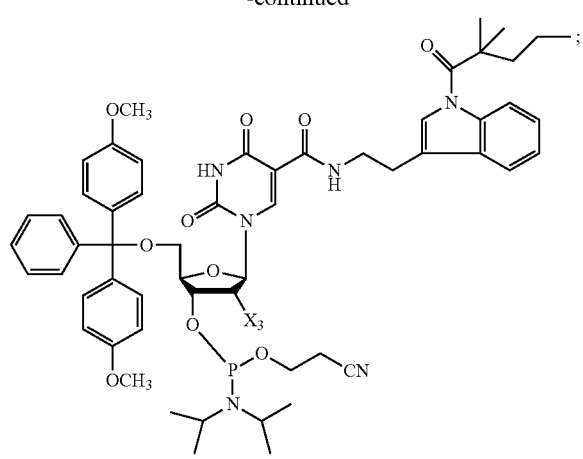
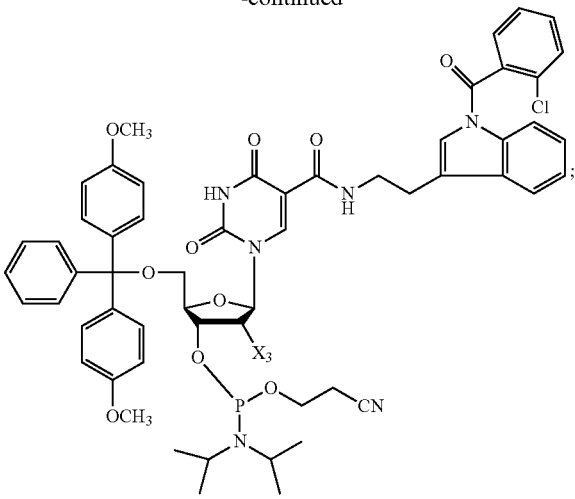
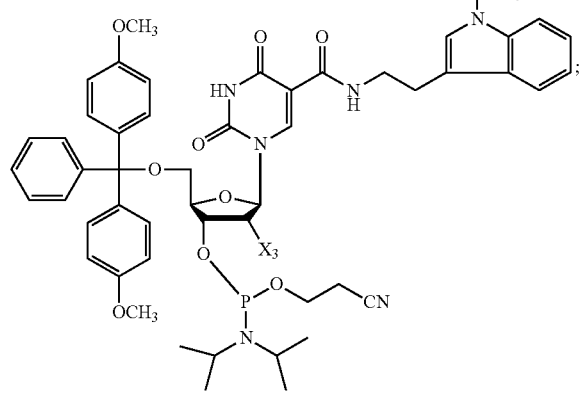
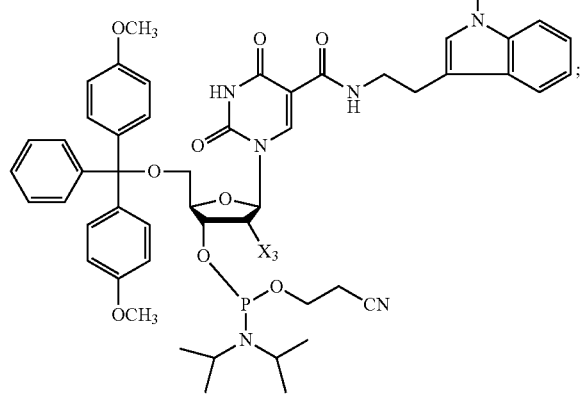
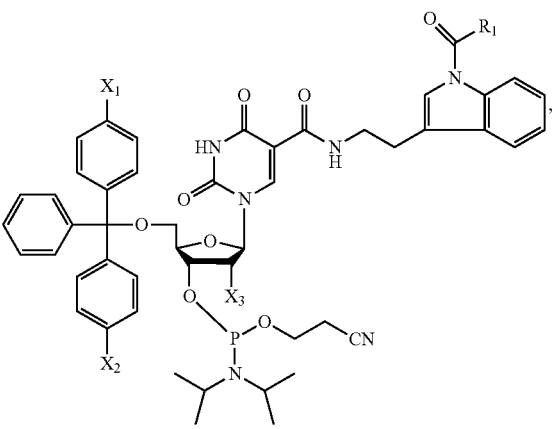
and salts thereof.
23. A method of producing a compound having the structure:
or a salt thereof
wherein,
R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

$X_1$ and $X_2$ are each independently selected from methoxy and hydrogen;

$X_3$ is selected from a methoxy, fluoro, hydrogen, and tert-butyldimethylsilyloxy;

comprising the steps of:

a) reacting N-α-BOC-tryptamine with an acid chloride selected from pivaloyl chloride, 2,2-dimethylbutyroyl chloride, 2,2-dimethylvaleroyl chloride, 1-methylcyclopentane-1-carbonyl chloride, 1-methylcyclohexane-1-carbonyl chloride, 2-chlorobenzoyl chloride, and 2-cyanobenzoyl chloride, to form the compound

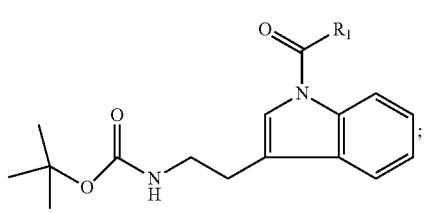

b) reacting the compound

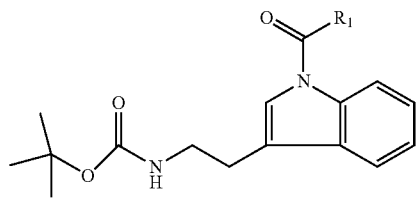

with trifluoroacetic acid to form the compound

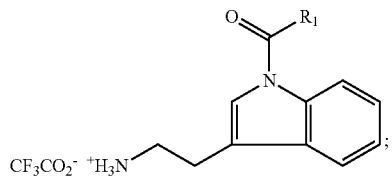

c) reacting the compound

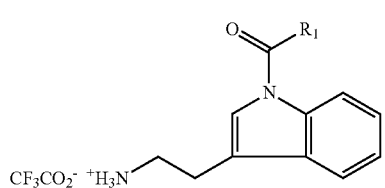

with 5'-O-DMT-5-(2,2,2-trifluoroethyoxy-carbonyl)-2'-deoxyuridine (TFEdU) to form the compound

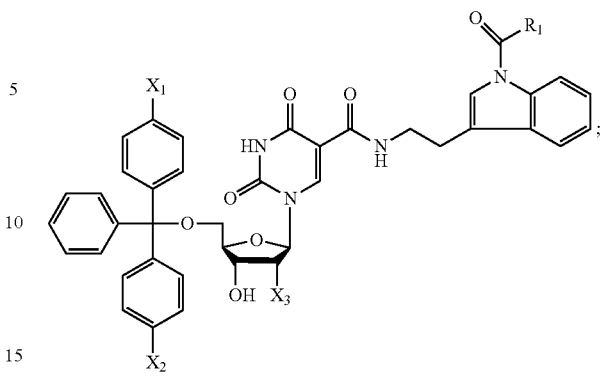

and d) reacting the compound

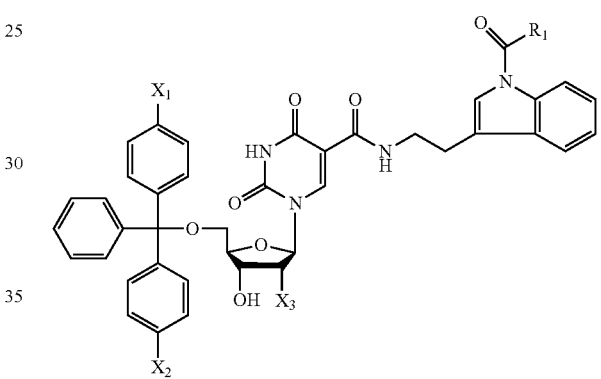

with 2 cyanoethyl-N,N,N',N'-tetraisopropylphosphoramidite.

24. The method of claim 23, wherein the method produces a compound selected from:

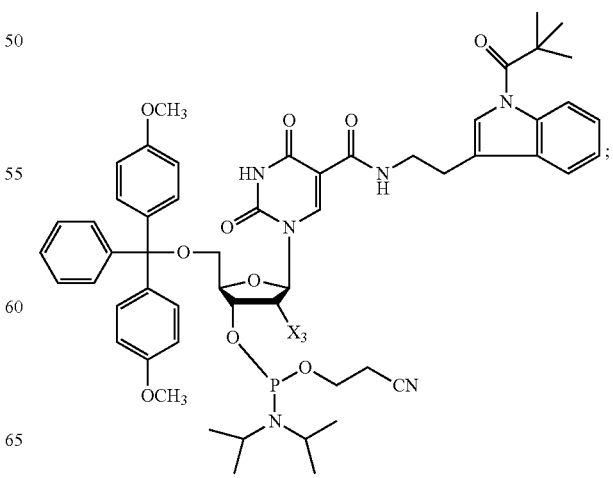

75
-continued
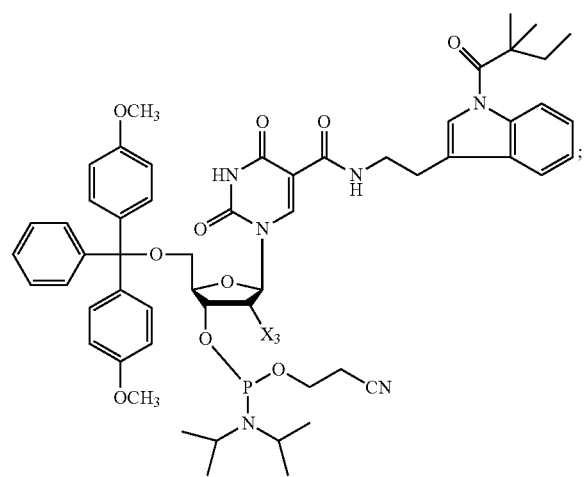
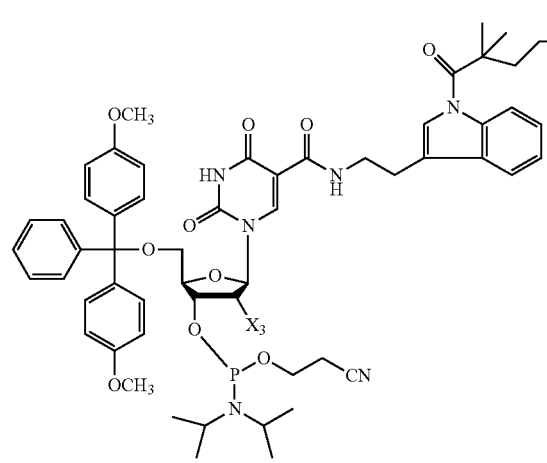
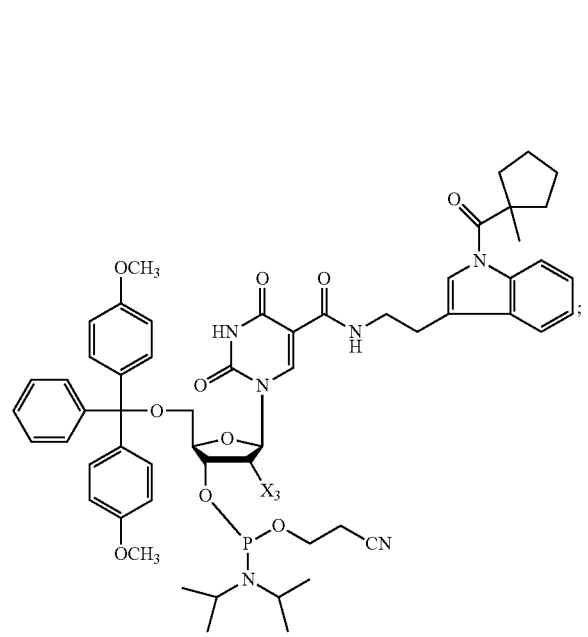
76
-continued
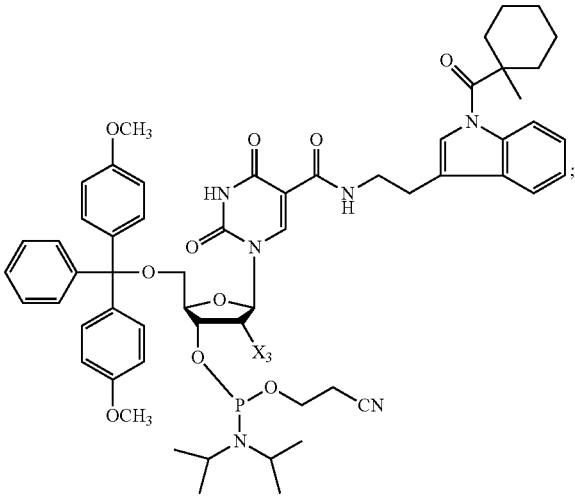
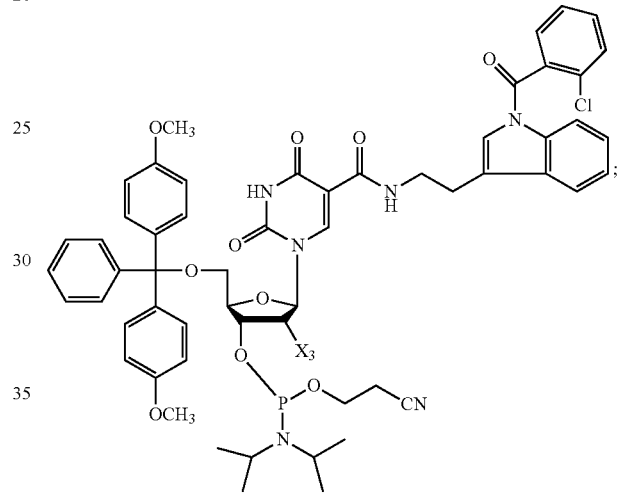
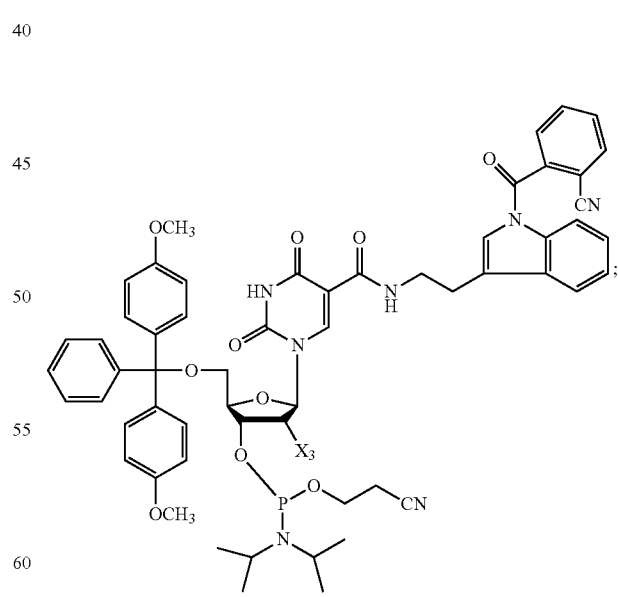
and salts thereof.
25. An oligonucleotide comprising at least one protected TrpU nucleotide, wherein at least one protected TrpU nucleotide in the oligonucleotide has the structure:

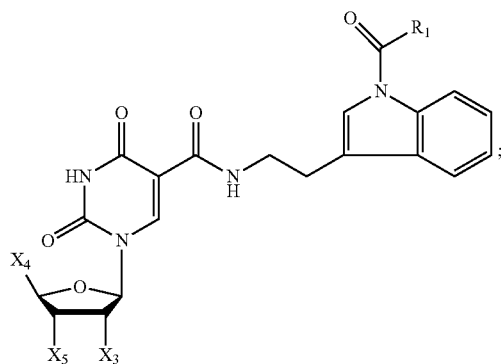

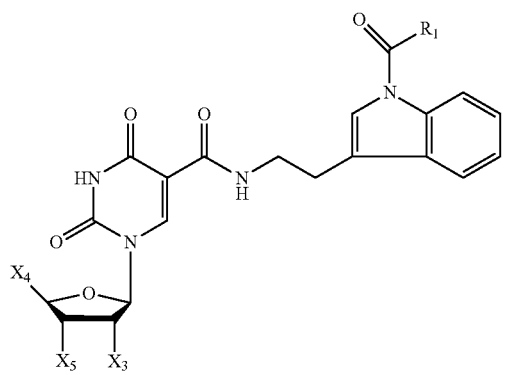

wherein,

R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

$X_3$ is selected from a methoxy, fluoro, hydrogen, and tert-butyldimethylsilyloxy;

$X_4$ is selected from OH, —OR, —SR, and —Z—P(Z')(Z")O—R, wherein Z, Z', and Z" are each independently selected from O and S, and R is an adjacent nucleotide in the oligonucleotide; and $X_5$ is selected from —O-ss, —OR, —SR, and —Z—P(Z')(Z")O—R, wherein ss is a solid support, Z, Z', and Z" are each independently selected from O and S, and R is an adjacent nucleotide in the oligonucleotide.

26. A method of producing an oligonucleotide comprising at least one TrpU nucleotide, comprising incorporating at least one nucleotide having the structure:

wherein,

R₁ is selected from tent-butyl, 1,1-dimethyl-propyl; 1,1-dimethyl-butyl; 2-chlorophenyl; 2-cyanophenyl; 1-methyl-cyclopentyl; and 1-methyl-cyclohexyl;

$X_3$ is selected from a methoxy, fluoro, hydrogen, and tert-butyldimethylsilyloxy;

$X_4$ is selected from OH, —OR, —SR, and —Z—P(Z')(Z")O—R, wherein Z, Z', and Z" are each independently selected from O and S, and R is an adjacent nucleotide in the oligonucleotide; and $X_5$ is selected from —O-ss, —OR, —SR, and —Z—P(Z')(Z")O—R, wherein ss is a solid support, Z, Z', and Z" are each independently selected from O and S, and R is an adjacent nucleotide in the oligonucleotide;

into a nucleotide sequence on a solid support; and removing the

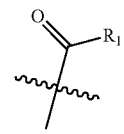

protecting group from the at least one TrpU nucleotide incorporated into the oligonucleotide.

* * * * *

UNITED STATES PATENT AND TRADEMARK OFFICE
CERTIFICATE OF CORRECTION

PATENT NO.         : 10,634,679 B2
APPLICATION NO.    : 16/078859
DATED              : April 28, 2020
INVENTOR(S)        : John Rohloff It is certified that error appears in the above-identified patent and that said Letters Patent is hereby corrected as shown below:

In the Claims

In Claim 1, at Column 58, Line 38, "tent-butyl" should read --tert-butyl--;

In Claim 3, at Column 61, Line 23, "tent-butyl" should read --tert-butyl--;

In Claim 5, at Column 63, Line 35, "tent-butyl" should read --tert-butyl--;

In Claim 7, at Column 63, Line 65, "tent-butyl" should read --tert-butyl--;

In Claim 9, at Column 64, Line 28, "tent-butyl" should read --tert-butyl--;

In Claim 10, at Column 64, Line 37, "tent-butyl" should read --tert-butyl--;

In Claim 12, at Column 64, Line 65, "tent-butyl" should read --tert-butyl--;

In Claim 14, at Column 65, Line 48, "tent-butyl" should read --tert-butyl--;

In Claim 18, at Column 68, Line 60, "tent-butyl" should read --tert-butyl--;

In Claim 23, at Column 72, Line 65, "tent-butyl" should read --tert-butyl--;

In Claim 25, at Column 77, Line 20, "tent-butyl" should read --tert-butyl--;

In Claim 26, at Column 78, Line 18, "tent-butyl" should read --tert-butyl--.

Signed and Sealed this
Fourteenth Day of July, 2020

Andrei Iancu
*Director of the United States Patent and Trademark Office*